(12) United States Patent
Agrawal et al.

(10) Patent No.: US 10,463,686 B2
(45) Date of Patent: Nov. 5, 2019

(54) IMMUNE MODULATION WITH TLR9 AGONISTS FOR CANCER TREATMENT

(71) Applicant: IDERA PHARMACEUTICALS, INC., Cambridge, MA (US)

(72) Inventors: Sudhir Agrawal, Shrewsbury, MA (US); Daqing Wang, Bedford, MA (US); Wayne Jiang, Waltham, MA (US)

(73) Assignee: IDERA PHARMACEUTICALS, INC., Exton, PA (US)

( * ) Notice: Subject to any disclaimer, the term of this patent is extended or adjusted under 35 U.S.C. 154(b) by 0 days.

(21) Appl. No.: 15/705,631

(22) Filed: Sep. 15, 2017

(65) Prior Publication Data
US 2018/0125877 A1    May 10, 2018

Related U.S. Application Data

(60) Provisional application No. 62/394,845, filed on Sep. 15, 2016, provisional application No. 62/486,738, filed on Apr. 18, 2017.

(51) Int. Cl.
| | | |
|---|---|---|
| *C07H 21/04* | (2006.01) | |
| *A61K 31/713* | (2006.01) | |
| *A61K 45/06* | (2006.01) | |
| *A61P 35/04* | (2006.01) | |
| *A61P 35/00* | (2006.01) | |
| *A61K 39/395* | (2006.01) | |
| *C07K 16/28* | (2006.01) | |
| *A61K 9/00* | (2006.01) | |

(52) U.S. Cl.
CPC ........ *A61K 31/713* (2013.01); *A61K 39/3955* (2013.01); *A61K 45/06* (2013.01); *A61P 35/00* (2018.01); *A61P 35/04* (2018.01); *C07K 16/2818* (2013.01); *A61K 9/0019* (2013.01); *C07K 2317/21* (2013.01); *C07K 2317/24* (2013.01)

(58) Field of Classification Search
CPC .................................................... A61K 48/00
See application file for complete search history.

(56) References Cited

U.S. PATENT DOCUMENTS

| | | | |
|---|---|---|---|
| 6,476,000 B1 | 11/2002 | Agrawal | |
| 7,250,403 B2 | 7/2007 | Van Nest et al. | |
| 7,276,489 B2 | 10/2007 | Agrawal et al. | |
| 7,427,405 B2 | 9/2008 | Agrawal et al. | |
| 7,470,674 B2 | 12/2008 | Agrawal et al. | |
| 7,709,617 B2 | 5/2010 | Kandimalla et al. | |
| 7,884,197 B2 | 2/2011 | Kandimalla et al. | |
| 7,960,362 B2 | 6/2011 | Kandimalla et al. | |
| 8,008,267 B2 | 8/2011 | Kandimalla et al. | |
| 8,158,768 B2 | 4/2012 | Dina et al. | |
| 8,361,986 B2 | 1/2013 | Kandimalla et al. | |
| 8,372,413 B2 | 2/2013 | Fearon et al. | |
| 2004/0214783 A1 | 10/2004 | Terman | |
| 2006/0074040 A1 | 4/2006 | Kandimalla | |
| 2008/0031887 A1 | 2/2008 | Lustgarten | |
| 2009/0117132 A1 | 5/2009 | Readett | |
| 2010/0166736 A1 | 7/2010 | Agrawal et al. | |
| 2011/0293565 A1 | 12/2011 | Kandimalla et al. | |
| 2013/0142815 A1 | 6/2013 | Ganapathy et al. | |
| 2015/0118222 A1 | 4/2015 | Levy et al. | |
| 2015/0273033 A1 | 10/2015 | Bosch et al. | |
| 2016/0101128 A1 | 4/2016 | Wang et al. | |

FOREIGN PATENT DOCUMENTS

| | | |
|---|---|---|
| WO | 2016030863 | 3/2016 |
| WO | 2016196062 | 5/2016 |
| WO | 2016128542 | 8/2016 |
| WO | 2016196173 | 12/2016 |

OTHER PUBLICATIONS

Mangsbo, Sara M., et al. "Enhanced tumor eradication by combining CTLA-4 or PD-1 blockade with CpG therapy." Journal of immunotherapy 33.3 (2010): 225-235.*

Duraiswamy, Jaikumar, Gordon J. Freeman, and George Coukos. "Therapeutic PD-1 pathway blockade augments with other modalities of immunotherapy T-cell function to prevent immune decline in ovarian cancer." Cancer research (2013).*

Brody, J.D., et al., "In Situ Vaccination with a TLR9 Agonist Induces Systemic Lymphoma Regression: a Phase I/II 'Study," J Clin Oncol., 28: 4324-4332 (2010).

Clinicaltrials.Gov Archive: Nct02254772 on Oct. 1 2014: Clinical Trials Identifier: Nct02254772 [Online]. U.S. 2 National Institute of Health. Oct. 1, 2014 [Retrieved on Dec. 30, 2015]. Retrieved From the Internet: <Url: Https://Clinicaltrials.Gov/Archive/Nct02254772/2014_10_01 >; pp. 1-5.

H. Poeck, et al., "Plasmacytoid Dendritic Cells, Antigen, and CpG-C License Human B Cells for Plasma Cell Differentiation and Immunoglobulin Production in the Absence of T-Cell Help", Blood, vol. 103, No. 8, (2004), pp. 3058-3064.

Hartmann, G., et al., "Rational Design of New CpG Oligonucleotides that Combine B Cell Activation with High IFN-Alpha Induction in Plasmacytoid Dendritic Cells", European Journal of Immunology, Wiley-V C H Verlag Gmbh & Co. KGAA, DE, vol. 33, No. 6, (2003), pp. 1633-1641.

Holzel et al. Plasticity of Tumour and Immune Cells: a Source of Heterogeneity and a Cause for Therapy Resistance? Nature Reviews. Cancer, 2013: 13:365-376.

Ito, H., et al., "Inhibition of Indoleamine 2,3-Dioxygenase Activity Enhances the Anti-Tumor Effects of a TLR7 Agonist in an Established Cancer Model," Accepted Article, Doi: 10.1111/Imm.12413.

International Search Report and Written Opinion, for International Application No. PCT/2017/051742, dated Dec. 18, 2017, 10 pages.

(Continued)

*Primary Examiner* — Kimberly Chong
(74) *Attorney, Agent, or Firm* — Morgan, Lewis & Bockius LLP

(57) ABSTRACT

The present invention relates to methods for treating a tumor, including a metastatic tumor, with TLR9 agonist in combination with an immune checkpoint inhibitor therapy.

24 Claims, 32 Drawing Sheets
Specification includes a Sequence Listing.

(56) References Cited

OTHER PUBLICATIONS

Kandimalla, E. R., et al., "Divergent Synthetic Nucleotide Motif Recognition Pattern: Design and Development of Potent Immunomodulatory Oligodeoxyribonucleotide Agents with Distinct Cytokine Induction Profiles", Nucleic Acids Research, Oxford University Press, GB, vol. 31, No. 9, (2003), pp. 2393-2400.

Kandimalla, E. R., et al., "Immunomodulatory Oligonucleotides Containing a Cytosine-Phosphate-2'-Deoxy-7-Deazaguanosine Motif as Potent Toll-Like Receptor 9 Agonists", Proceedings of the National Academy of Sciences, National Academy of Sciences, US, vol. 102, No. 19, (2005), pp. 6925-6930.

Kim, Y. H., et al., "In Situ Vaccination Against Mycosis Fungoides by Intratumoral Injection of a TLR9 Agonist Combined with Radiation: a Phase 1/2 Study," Blood, 119(2): 355-363 (2012).

Liu, Q., et al., "Changes in the PD-1 and PD-L1 Expressions of Splenic Dendritic Cells in Multiple-Organ Dysfunction Syndrome Mice and Their Significance," Genetics and Molecular Research 13 (3): 7666-7672 (2014).

Lou Y., et al., "Antitumor Activity Mediated by CpG: The Route of Administration is Critical," J. Immunother, 34(3): 279-288 (2011).

Lu, H., "TLR Agonists for Cancer Immunotherapy: Tipping the Balance Between the Immune Stimulatory and Inhibitory Effects" Frontiers in Immunotherapy, 5(83): 1-4 (2014).

Marabelle, A., et al., "Depleting Tumor-Specific Tregs at a Single Site Eradicates Disseminated Tumors," J. Clin. Invest. 2013; 123(6):2447-2463.

Marabelle, A., et al., "Intratumoral Anti-CTLA-4 Therapy: Enhancing Efficacy While Avoiding Toxicity," Clin Cancer Res: 19(19); 5261-3 (2013).

Margolin et al., "Ipilimumab in Patients with Melanoma and Brain Metastases: an open-label, phase 2 trial", Lancet May 2012,13, pp. 459-465.

Marshall, J. D., et al., "Identification of a Novel CpG DNA Class and Motif That Optimally Stimulate B Cell and Plasmacytoid Dendritic Cell Functions", Journal of Leukocyte Biology, Federation of American Societies for Experimental Biology, US, vol. 73, No. 6, (2003), pp. 781-792.

Millward, M. et al., "Phase I Study of Tremelimumab (Cp-675 206) Plus Pf-3512676 (CpG 7909) in Patients with Melanoma or Advanced Solid Tumours," British J. of Cancer, 108: 1998-2004 (2013).

Pardoll, DM, "The blockade of immune checkpoints in cancer immunotherapy". National Review Cancer. Apr. 2012, Epub Mar. 22, 2012, vol. 12, No. 4; pp. 252-264.

Shirota, Y., et al., "Intratumoral Injection of CpG Oligonucleotides Induces the Differentiation and Reduces the Immunosuppressive Activity of Myeloid-Derived Suppressor Cells," The Journal of Immunology, 188: 1592-1599 (2012).

Singh, M., et al., "Effective Innate and Adaptive Antimelanoma Immunity Through Localized TLR7/8 Activation," The Journal of Immunology, 193: 4722-4731 (2014).

Webster, W. S., et al., "Targeting Molecular and Cellular Inhibitory Mechanisms for Improvement of Antitumor Memory Responses Reactivated by Tumor Cell Vaccine," J. Immunol, 179: 2860-2869 (2007).

Wolfle, S., J., et al., "PD-L1 Expression on Tolerogenic Apcs is Controlled by Stat-3," Supplement, Eur. J. Immunol., 41: 413-424 (2011).

Yu, D., et al., "Impact of Secondary Structure of Toll-Like Receptor 9 Agonists on Interferon Alpha Induction," Antimicrobial Agents and Chemotherapy, 52(12): 4320-4325 (2008).

Ng, J., et al., "Radiation therapy and the abscopal effect: a concept comes of age," Ann. Transl. Med. 2016; 4(6):118.

Extended European Search Report for EP Application No. 15848691. 0, dated Mar. 9, 2018, 9 pages.

Idera Pharmaceuticals. "U.S. FDA Grants Fast Track Designation for Idera Pharmaceuticals IMO-2125 in Combination with Ipilmumab for Treatment of PD-1 Refractory Metastatic Melanoma." Investors Press Release dated Nov. 29, 2017. http ://ir .i derapharma. com/ news-rel eases/news-rel ease-detail s/us-f da-grants-fast-track-desig . . . accessed May 18, 2018.

Daqing Wang, Dong Yu, Sudhir Agrawal. Intratumoral injection of IMO-2055, a novel Toll-like receptor 9 agonist, with ipilimumab induces a systemic tumor-specific immune response. [abstract]. In: Proceedings of the AACR Special Conference: Tumor Immunology and Immunotherapy: A New Chapter; Dec. 1-4, 2014; Orlando, FL. Philadelphia (PA): AACR; Cancer Immunol Res 2015;3(10 Suppl):Abstract nr A56.

* cited by examiner

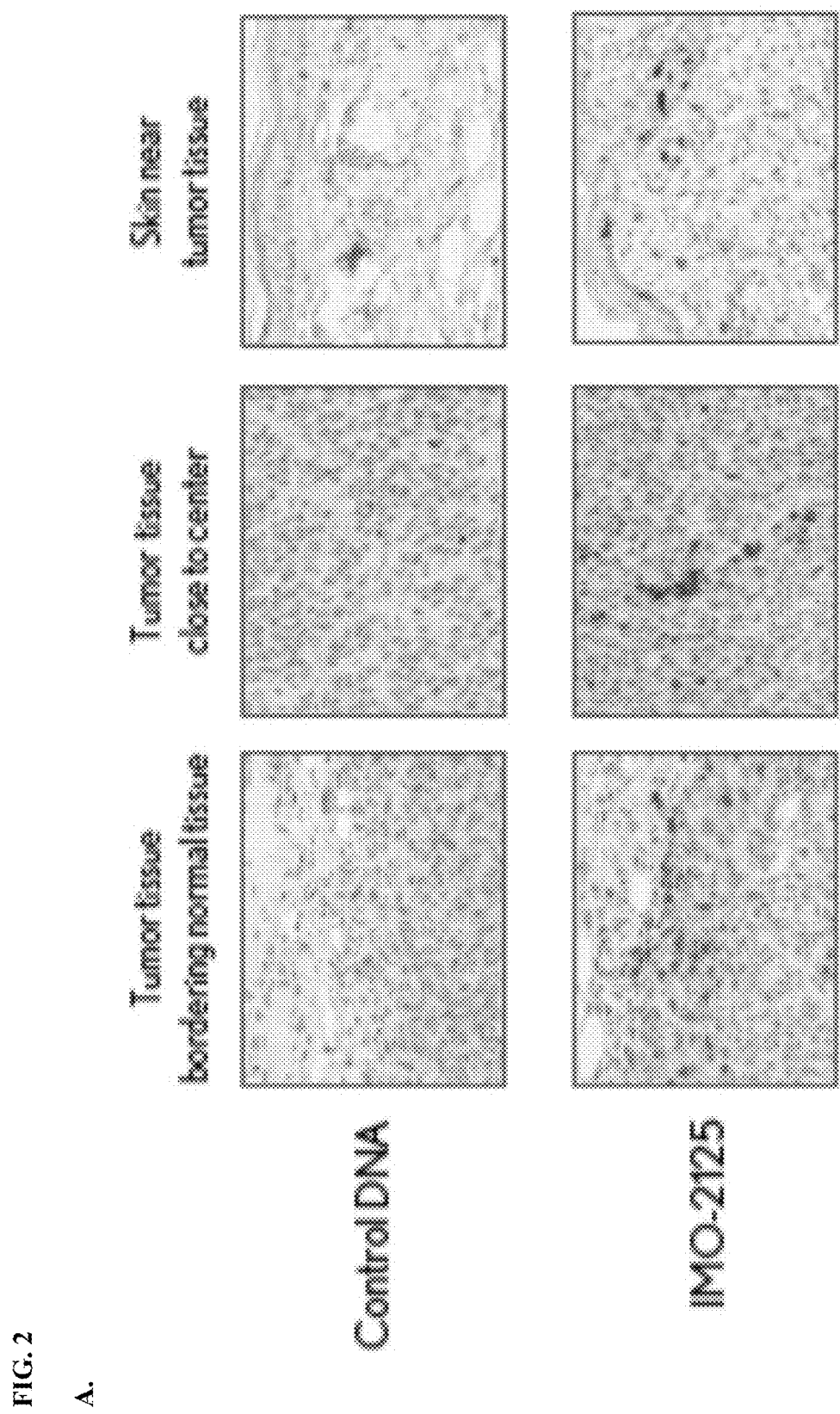

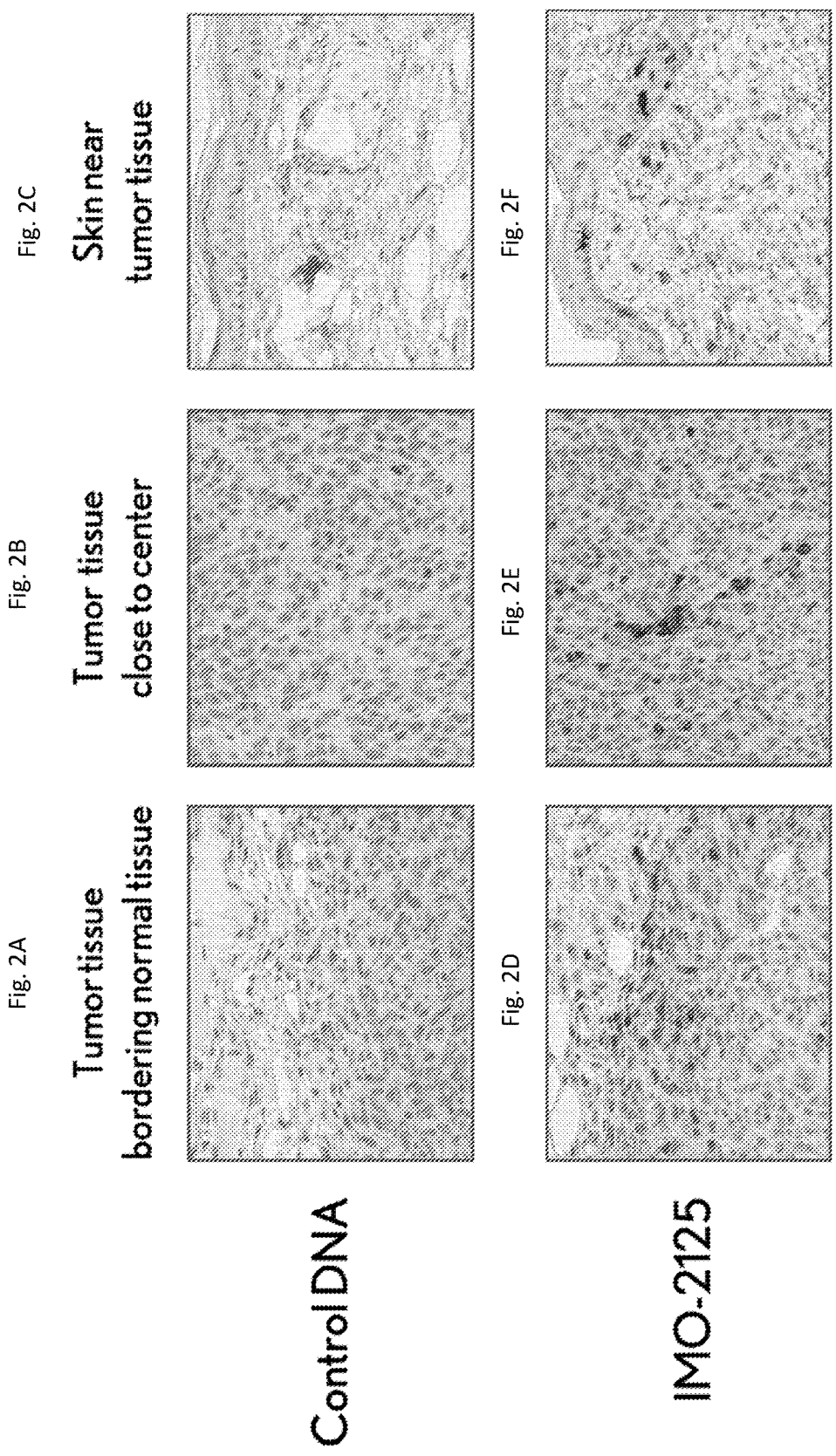

B.

B.

A.

B.

Anti-tumor activity correlated with increased infiltration of TILs
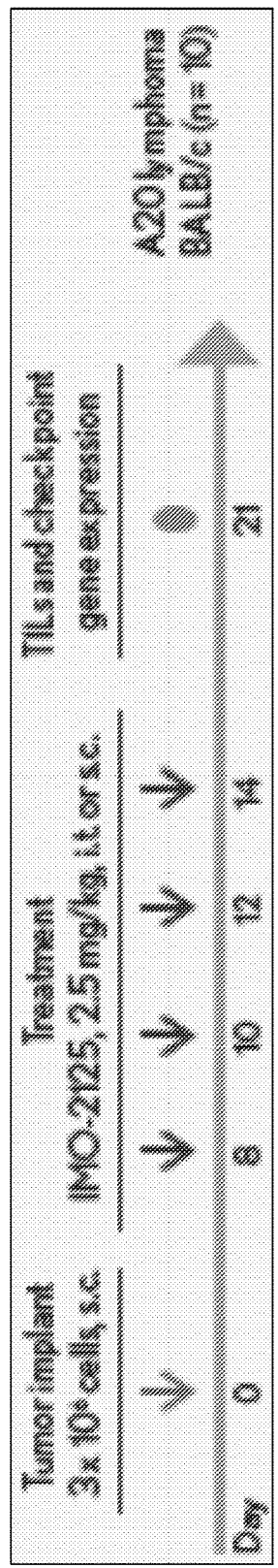
FIG. 6A
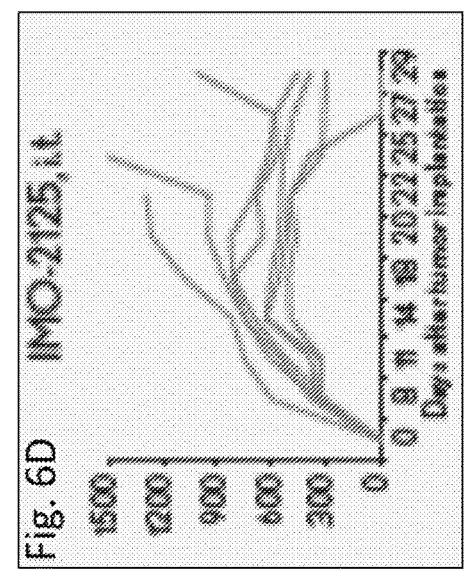
Fig. 6D INO-2125, i.t.
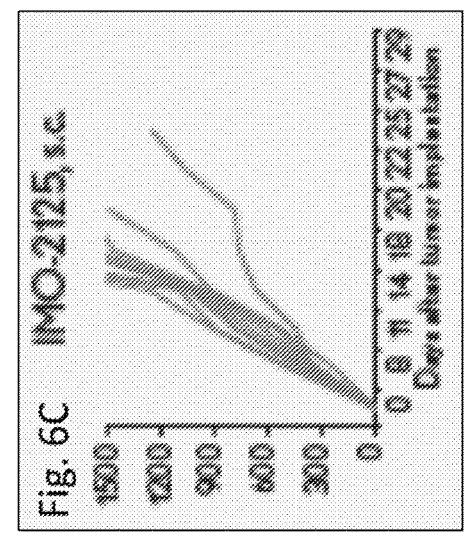
Fig. 6C INO-2125, s.c.
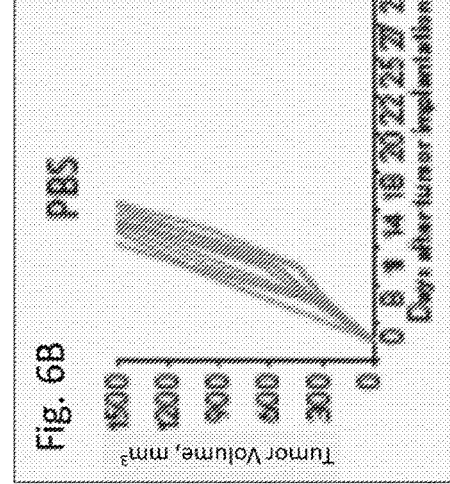
Fig. 6B PBS

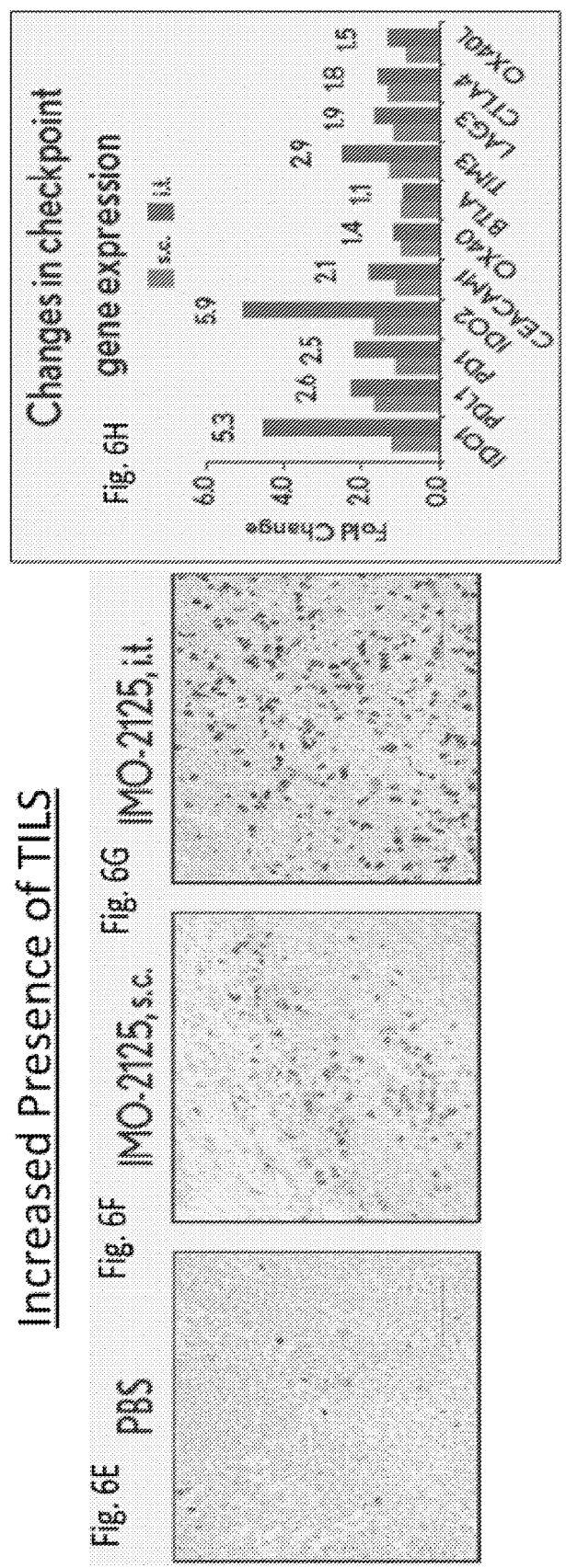

B.

B.

A.

B.

C.

B.

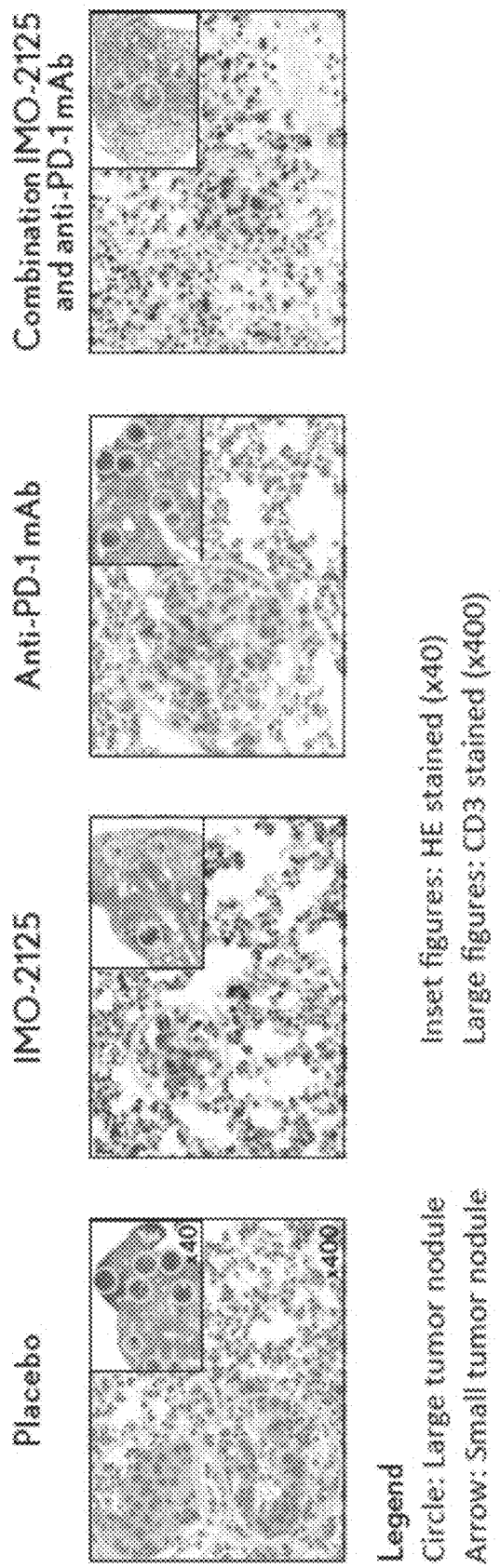

SEQUENCE LISTING

```
<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (16)..(16)
<223> OTHER INFORMATION: 2'-deoxy-7-deazaguanosine

<400> SEQUENCE: 1
tctgacgttc ttcttgcagt ct                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (16)..(16)
<223> OTHER INFORMATION: 2'-deoxy-7-deazaguanosine
```

```
<400> SEQUENCE: 2
tctgtcgttc ttcttgctgt ct                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (17)..(17)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 3
tcgtcgttct ggtcttgctg ct                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by is a glycerol linker
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (12)..(12)
<223> OTHER INFORMATION: 2'-deoxy-7-deazaguanosine
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 4
tcgaacgttc ggcttgcaag ct                                              22

<210> SEQ ID NO 5
```

```
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: phosphodiester linkage
<220> FEATURE:
<221> NAME/KEY: misc_feature
<222> LOCATION: (6)..(6)
<223> OTHER INFORMATION: 2'-deoxy-arabinoguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (17)..(17)
<223> OTHER INFORMATION: 2'-deoxy-arabinoguanosine
<220> FEATURE:
<221> NAME/KEY: misc_feature
<222> LOCATION: (18)..(18)
<223> OTHER INFORMATION: Phosphodiester linkage

<400> SEQUENCE: 5
ctgtcgttct cctcttgctg tc                                            22

<210> SEQ ID NO 6
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (6)..(6)
<223> OTHER INFORMATION: 2'-deoxy-arabinoguanosine
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (12)..(12)
<223> OTHER INFORMATION: Phosphodiester linkage
<220> FEATURE:
<221> NAME/KEY: misc_feature
<222> LOCATION: (17)..(17)
<223> OTHER INFORMATION: 2'-deoxy-arabinoguanosine

<400> SEQUENCE: 6
ctgtcgttct cctcttgctg tc                                            22

<210> SEQ ID NO 7
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
```

```
<222> LOCATION: (11)..(12)
<223> OTHER INFORMATION: Linked by a glycerol linker
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (16)..(16)
<223> OTHER INFORMATION: 2'-deoxy-arabinoguanosine

<400> SEQUENCE: 7
tcgaacgttc gtcttgctgt ct                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a C3-linker
<220> FEATURE:
<221> NAME/KEY: misc_feature
<222> LOCATION: (16)..(16)
<223> OTHER INFORMATION: 2'-deoxy-7-deazaguanosine

<400> SEQUENCE: 8
tcgaacgttc ggacagctgt ct                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (6)..(6)
<223> OTHER INFORMATION: 2'-deoxy-arabinoguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (17)..(17)
<223> OTHER INFORMATION: 2'-deoxy-arabinoguanosine

<400> SEQUENCE: 9
cagtcgttca ggacttgctg ac                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: (6)..(6)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (17)..(17)
<223> OTHER INFORMATION: 2'-deoxy-7-deazaguanosine

<400> SEQUENCE: 10
cagtcgttca ggacttgctg ac                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: 2'-O-methylribonucleotide
<220> FEATURE:
<221> NAME/KEY: misc_feature
<222> LOCATION: (11)..(12)
<223> OTHER INFORMATION: Linked by a 1,3,5-pentanetriol linker
<220> FEATURE:
<221> NAME/KEY: misc_feature
<222> LOCATION: (12)..(12)
<223> OTHER INFORMATION: 2'-O-methylribonucleotide
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 11
tcgaacgttc ggcttgcaag ct                                              22

<210> SEQ ID NO 12
<211> LENGTH: 26
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
```

```
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a 1,3-propanediol linker
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: 2'-O-methylribonucleotide
<220> FEATURE:
<221> NAME/KEY: misc_feature
<222> LOCATION: (24)..(24)
<223> OTHER INFORMATION: 2'-deoxy-7-deazaguanosine

<400> SEQUENCE: 12
tcgaacgttc gtcttgctgt cttgct                                              26

<210> SEQ ID NO 13
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a 1,3-propanediol linker
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-O-methylribonucleotide

<400> SEQUENCE: 13
tcgaacgttc gtcttgctgu ct                                                  22

<210> SEQ ID NO 14
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (8)..(8)
```

```
<223> OTHER INFORMATION: a phosphodiester linkage
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: 2'-O-methylribonucleotide
<220> FEATURE:
<221> NAME/KEY: misc_feature
<222> LOCATION: (11)..(12)
<223> OTHER INFORMATION: Linked by a cis,trans-1,3,5-cyclohexanetriol
      linker
<220> FEATURE:
<221> NAME/KEY: misc_feature
<222> LOCATION: (12)..(12)
<223> OTHER INFORMATION: 2'-O-methylribonucleotide
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (14)..(14)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 14
tcgaacgttc ggcttgcaag ct                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: 2'-O-methylribonucleotide
<220> FEATURE:
<221> NAME/KEY: misc_feature
<222> LOCATION: (11)..(12)
<223> OTHER INFORMATION: Linked by a 1,4-butanediol linker
<220> FEATURE:
<221> NAME/KEY: misc_feature
<222> LOCATION: (17)..(17)
<223> OTHER INFORMATION: 2'-deoxy-arabinoguanosine

<400> SEQUENCE: 15
tcgaacgttc ggacttgctg ac                                              22

<210> SEQ ID NO 16
<211> LENGTH: 26
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: 2'-O-methylribonucleotide
<220> FEATURE:
<221> NAME/KEY: misc_feature
<222> LOCATION: (24)..(24)
<223> OTHER INFORMATION: 2'-deoxy-7-deazaguanosine

<400> SEQUENCE: 16
tcgaacgttc gtgttgctgt cttgct                                          26

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-arabinoguanosine
<220> FEATURE:
<221> NAME/KEY: misc_feature
<222> LOCATION: (6)..(6)
<223> OTHER INFORMATION: 2'-deoxy-arabinoguanosine
<220> FEATURE:
<221> NAME/KEY: misc_feature
<222> LOCATION: (9)..(9)
<223> OTHER INFORMATION: 2'-deoxy-U
<220> FEATURE:
<221> NAME/KEY: misc_feature
<222> LOCATION: (10)..(11)
<223> OTHER INFORMATION: Linked by a cis,cis-1,3,5-cyclohexanetriol
      linker
<220> FEATURE:
<221> NAME/KEY: misc_feature
<222> LOCATION: (12)..(12)
<223> OTHER INFORMATION: 2'-deoxy-U
<220> FEATURE:
<221> NAME/KEY: misc_feature
<222> LOCATION: (14)..(14)
<223> OTHER INFORMATION: 2'-deoxy-arabinoguanosine
<220> FEATURE:
<221> NAME/KEY: misc_feature
<222> LOCATION: (17)..(17)
<223> OTHER INFORMATION: 2'-deoxy-arabinoguanosine

<400> SEQUENCE: 17
tcgtcgttuy yuttgctgct                                                 20

<210> SEQ ID NO 18
<211> LENGTH: 22
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: misc_feature
<222> LOCATION: (6)..(6)
<223> OTHER INFORMATION: 2'-deoxy-arabinoguanosine
<220> FEATURE:
<221> NAME/KEY: misc_feature
<222> LOCATION: (11)..(12)
<223> OTHER INFORMATION: Linked by a 1,4-butanediol linker
<220> FEATURE:
<221> NAME/KEY: misc_feature
<222> LOCATION: (16)..(16)
<223> OTHER INFORMATION: 2'-deoxy-7-deazaguanosine

<400> SEQUENCE: 18
cagtcgttca gtcttgctgt ct                                               22

<210> SEQ ID NO 19
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a glycerol linker
<220> FEATURE:
<221> NAME/KEY: misc_feature
<222> LOCATION: (12)..(12)
<223> OTHER INFORMATION: 2'-deoxy-7-deazaguanosine
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 19
tcgtacgtac ggcatgcatg ct                                               22

<210> SEQ ID NO 20
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a 1,3,5-pentanetriol linker
<220> FEATURE:
<221> NAME/KEY: misc_feature
```

```
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 20
tcgaacgttc ggcttgcaag ct                                              22

<210> SEQ ID NO 21
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(12)
<223> OTHER INFORMATION: Linked by a 1,4-butanediol linker
<220> FEATURE:
<221> NAME/KEY: misc_feature
<222> LOCATION: (15)..(15)
<223> OTHER INFORMATION: 2'-deoxy-arabinoguanosine
<220> FEATURE:
<221> NAME/KEY: misc_feature
<222> LOCATION: (23)..(23)
<223> OTHER INFORMATION: 2'-deoxy-7-deazaguanosine

<400> SEQUENCE: 21
tcgaacgttc gcttgctgac ttgct                                           25

<210> SEQ ID NO 22
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: a phosphodiester linkage
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a isobutanetriol linker
<220> FEATURE:
<221> NAME/KEY: misc_feature
<222> LOCATION: (12)..(12)
<223> OTHER INFORMATION: 2'-deoxy-7-deazaguanosine
<220> FEATURE:
```

<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 22
tcgaacgttc ggcttgcaag ct                                            22

<210> SEQ ID NO 23
<211> LENGTH: 26
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a 1,5-pentandiol linker
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (24)..(24)
<223> OTHER INFORMATION: 2'-deoxy-7-deazaguanosine

<400> SEQUENCE: 23
tcgaacgttc gcattgctgt cttgct                                        26

<210> SEQ ID NO 24
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a cis,trans-1,3,5-cyclohexanetriol
      linker
<220> FEATURE:
<221> NAME/KEY: misc_feature
<222> LOCATION: (12)..(12)
<223> OTHER INFORMATION: 2'-deoxy-7-deazaguanosine
<220> FEATURE:
<221> NAME/KEY: misc_feature
<222> LOCATION: (16)..(16)

<223> OTHER INFORMATION: 2'-deoxy-7-deazaguanosine
<220> FEATURE:
<221> NAME/KEY: misc_feature
<222> LOCATION: (20)..(20)
<223> OTHER INFORMATION: 2'-deoxy-7-deazaguanosine

<400> SEQUENCE: 24
tcgaacgttc ggcttgcaag ct                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a isobutanetriol linker
<220> FEATURE:
<221> NAME/KEY: misc_feature
<222> LOCATION: (12)..(12)
<223> OTHER INFORMATION: a phosphodiester linkage
<220> FEATURE:
<221> NAME/KEY: misc_feature
<222> LOCATION: (12)..(12)
<223> OTHER INFORMATION: 2'-deoxy-7-deazaguanosine
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (17)..(17)
<223> OTHER INFORMATION: a phosphodiester linkage
<220> FEATURE:
<221> NAME/KEY: misc_feature
<222> LOCATION: (20)..(20)
<223> OTHER INFORMATION: a phosphodiester linkage
<220> FEATURE:
<221> NAME/KEY: misc_feature
<222> LOCATION: (20)..(20)
<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: a phosphodiester linkage

<400> SEQUENCE: 25
tcgaacgttc ggcttgcaag ct                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (8)..(8)
<223> OTHER INFORMATION: a phosphodiester linkage
<220> FEATURE:
<221> NAME/KEY: misc_feature
<222> LOCATION: (9)..(9)
<223> OTHER INFORMATION: a phosphodiester linkage
<220> FEATURE:
<221> NAME/KEY: misc_feature
<222> LOCATION: (9)..(9)
<223> OTHER INFORMATION: 2'-deoxy-7-deazaguanosine
<220> FEATURE:
<221> NAME/KEY: misc_feature
<222> LOCATION: (9)..(10)
<223> OTHER INFORMATION: Linked by an isobutanetriol linker
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (10)..(10)
<223> OTHER INFORMATION: 2'-deoxy-7-deazaguanosine
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (15)..(15)
<223> OTHER INFORMATION: a phosphodiester linkage
<220> FEATURE:
<221> NAME/KEY: misc_feature
<222> LOCATION: (18)..(18)
<223> OTHER INFORMATION: a phosphodiester linkage
<220> FEATURE:
<221> NAME/KEY: misc_feature
<222> LOCATION: (18)..(18)
<223> OTHER INFORMATION: 2'-deoxy-7-deazaguanosine
<220> FEATURE:

<221> NAME/KEY: misc_feature
<222> LOCATION: (20)..(20)
<223> OTHER INFORMATION: a phosphodiester linkage

<400> SEQUENCE: 26
tcgaacgttc ggcttgcaag ct                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(11)
<223> OTHER INFORMATION: 2'-deoxy-7-deazaguanosine
<220> FEATURE:
<221> NAME/KEY: misc_feature
<222> LOCATION: (11)..(12)
<223> OTHER INFORMATION: Linked by a cis,trans-1,3,5-cyclohexanetriol
      linker
<220> FEATURE:
<221> NAME/KEY: misc_feature
<222> LOCATION: (12)..(12)
<223> OTHER INFORMATION: a phosphodiester linkage
<220> FEATURE:
<221> NAME/KEY: misc_feature
<222> LOCATION: (12)..(12)
<223> OTHER INFORMATION: 2'-deoxy-7-deazaguanosine
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (17)..(17)
<223> OTHER INFORMATION: a phosphodiester linkage
<220> FEATURE:
<221> NAME/KEY: misc_feature
<222> LOCATION: (20)..(20)
<223> OTHER INFORMATION: a phosphodiester linkage
<220> FEATURE:
<221> NAME/KEY: misc_feature
<222> LOCATION: (20)..(20)

<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: a phosphodiester linkage

<400> SEQUENCE: 27
tcgaacgttc ggcttgcaag ct                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-arabinoguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-arabinoguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(11)
<223> OTHER INFORMATION: 2'-deoxy-arabinoguanosine
<220> FEATURE:
<221> NAME/KEY: misc_feature
<222> LOCATION: (11)..(12)
<223> OTHER INFORMATION: Linked by an isobutanetriol linker
<220> FEATURE:
<221> NAME/KEY: misc_feature
<222> LOCATION: (12)..(12)
<223> OTHER INFORMATION: a phosphodiester linkage
<220> FEATURE:
<221> NAME/KEY: misc_feature
<222> LOCATION: (12)..(12)
<223> OTHER INFORMATION: 2'-deoxy-arabinoguanosine
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-arabinoguanosine
<220> FEATURE:
<221> NAME/KEY: misc_feature
<222> LOCATION: (17)..(17)
<223> OTHER INFORMATION: a phosphodiester linkage
<220> FEATURE:
<221> NAME/KEY: misc_feature
<222> LOCATION: (20)..(20)
<223> OTHER INFORMATION: a phosphodiester linkage
<220> FEATURE:
<221> NAME/KEY: misc_feature
<222> LOCATION: (20)..(20)
<223> OTHER INFORMATION: 2'-deoxy-arabinoguanosine
<220> FEATURE:
<221> NAME/KEY: misc_feature
<222> LOCATION: (21)..(21)
<223> OTHER INFORMATION: a phosphodiester linkage

<400> SEQUENCE: 28
tcgaacgttc ggcttgcaag ct                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(12)
<223> OTHER INFORMATION: Linked by a 1,3,5-pentanetriol linker
<220> FEATURE:
<221> NAME/KEY: misc_feature
<222> LOCATION: (12)..(12)
<223> OTHER INFORMATION: a phosphodiester linkage
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (17)..(17)
<223> OTHER INFORMATION: a phosphodiester linkage
<220> FEATURE:
<221> NAME/KEY: misc_feature
<222> LOCATION: (20)..(20)
<223> OTHER INFORMATION: a phosphodiester linkage
<220> FEATURE:
<221> NAME/KEY: misc_feature
<222> LOCATION: (20)..(20)
<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: a phosphodiester linkage

<400> SEQUENCE: 29
tcgaacgttc ggcttgcaag ct        22

<210> SEQ ID NO 30
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: a phosphodiester linkage
<220> FEATURE:
<221> NAME/KEY: misc_feature
<222> LOCATION: (3)..(3)
<223> OTHER INFORMATION: a phosphodiester linkage
<220> FEATURE:
<221> NAME/KEY: misc_feature
<222> LOCATION: (3)..(3)
<223> OTHER INFORMATION: 2'-deoxy-7-deazaguanosine
<220> FEATURE:
<221> NAME/KEY: misc_feature
<222> LOCATION: (6)..(6)
<223> OTHER INFORMATION: a phosphodiester linkage
<220> FEATURE:
<221> NAME/KEY: misc_feature
<222> LOCATION: (7)..(7)
<223> OTHER INFORMATION: 2'-deoxy-7-deazaguanosine
<220> FEATURE:
<221> NAME/KEY: misc_feature
<222> LOCATION: (10)..(10)
<223> OTHER INFORMATION: a phosphodiester linkage
<220> FEATURE:
<221> NAME/KEY: misc_feature
<222> LOCATION: (11)..(11)
<223> OTHER INFORMATION: a phosphodiester linkage
<220> FEATURE:
<221> NAME/KEY: misc_feature
<222> LOCATION: (11)..(12)
<223> OTHER INFORMATION: Linked by a 1,3,5-pentanetriol linker
<220> FEATURE:
<221> NAME/KEY: misc_feature
<222> LOCATION: (12)..(12)
<223> OTHER INFORMATION: a phosphodiester linkage
<220> FEATURE:
<221> NAME/KEY: misc_feature
<222> LOCATION: (13)..(13)
<223> OTHER INFORMATION: a phosphodiester linkage
<220> FEATURE:
<221> NAME/KEY: misc_feature
<222> LOCATION: (16)..(16)
<223> OTHER INFORMATION: 2'-deoxy-7-deazaguanosine
<220> FEATURE:
<221> NAME/KEY: misc_feature
<222> LOCATION: (17)..(17)
<223> OTHER INFORMATION: a phosphodiester linkage
<220> FEATURE:
<221> NAME/KEY: misc_feature
<222> LOCATION: (20)..(20)
<223> OTHER INFORMATION: a phosphodiester linkage
<220> FEATURE:
<221> NAME/KEY: misc_feature
<222> LOCATION: (20)..(20)
<223> OTHER INFORMATION: 2'-deoxy-7-deazaguanosine
<220> FEATURE:
<221> NAME/KEY: misc_feature
<222> LOCATION: (21)..(21)
<223> OTHER INFORMATION: a phosphodiester linkage

<400> SEQUENCE: 30
tcgaacgttc ggcttgcaag ct        22

IMMUNE MODULATION WITH TLR9 AGONISTS FOR CANCER TREATMENT

PRIORITY

This Application claims priority to, and the benefit of, U.S. Provisional Application No. 62/394,845 filed Sep. 15, 2016, and U.S. Provisional Application No. 62/486,738 filed Apr. 18, 2017, each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 105968-5001_Sequence_Listing, date recorded: Sep. 15, 2107; file size: 26 KB).

FIELD

The invention relates to the field of oncology, and use of immunotherapy in the treatment of cancer.

BACKGROUND

Toll-like receptors (TLRs) are present on many cells of the immune system and are involved in the innate immune response. In vertebrates, this family consists of eleven proteins called TLR1 to TLR11 that recognize pathogen associated molecular patterns from bacteria, fungi, parasites, and viruses. TLRs are a key mechanism by which vertebrates recognize and mount immune responses to foreign molecules and also provide a link between the innate and adaptive immune responses. Some TLRs are located on the cell surface to detect and initiate a response to extracellular pathogens and other TLRs are located inside the cell to detect and initiate a response to intracellular pathogens.

TLR9 recognizes unmethylated CpG motifs in bacterial DNA and in synthetic oligonucleotides. While agonists of TLR9, and other TLR agonists, can initiate anti-tumor immune responses, TLR agonists can also induce immune suppressive factors that may be counterproductive for effective tumor responses.

There is a need for cancer immunotherapies that induce antitumor responses, and keep the immune system productively engaged to improve the overall response.

SUMMARY

In various aspects, the present invention provides a method for treating a tumor, including, without limitation, metastatic melanoma, comprising intratumorally administering an oligonucleotide TLR9 agonist (e.g., IMO-2125 or other immunostimulatory oligonucleotides described herein) to a cancer patient in combination with immunotherapy with an immune checkpoint inhibitor therapy, such as a therapy targeting CTLA-4, PD-1/PD-L1/PD-L2, TIM3, LAG3, and/or IDO. The TLR9 agonist upon intratumoral injection induces global increases in expression of checkpoint genes, including IDO1, PDL1, PD1, IDO2, CEACAM1, OX40, TIM3, LAG3, CTLA4, and OX40L. By altering immune signaling in the tumor microenvironment, such changes in gene expression provide opportunities to improve responsiveness to checkpoint inhibitor therapy, including in some embodiments, a complete response. The invention further provides the opportunity to balance anti-tumor responses with inhibitory signals, thereby also minimizing immune-related adverse events (irAEs) of checkpoint inhibitor therapy.

In various embodiments, the patient has a cancer that was previously unresponsive to, or had become resistant to, a checkpoint inhibitor therapy, such as anti-CTLA-4, anti-PD-1, or anti-PD-L1 and/or anti-PD-L2 agent. The invention finds use for treating primary cancer or a metastatic cancer, including cancers that originate from skin, colon, breast, or prostate, among other tissues. In some embodiments, the cancer is progressive, locally advanced, or metastatic carcinoma. In some embodiments, the cancer is metastatic melanoma.

In accordance with embodiments of the invention, the immunostimulatory oligonucleotide (e.g., IMO-2125) is administered intratumorally. Intratumoral administration alters immune signaling in the tumor microenvironment, priming the immune system for an effective anti-tumor response, while inducing changes that are compatible with more effective checkpoint inhibitor therapy. For example, the TLR9 agonist (e.g., IMO-2125) may be administered intratumorally at from about 4 mg to about 64 mg per dose, with from about 3 to about 12 doses being administered over 10 to 12 weeks. For example, therapy may be initiated with 3 to 5 weekly doses of IMO-2125, optionally followed by 3 to 8 maintenance doses, which are administered about every three weeks.

During the regimen of IMO-2125 (or other TLR9 agonist), one or more checkpoint inhibitor therapies are administered to take advantage of the changes in immune signaling. In some embodiments, the patient receives an anti-CTLA-4 agent (e.g., ipilimumab or tremelimumab) and/or an anti-PD-1 agent (e.g., nivolumab or pembrolizumab). The immune checkpoint inhibitor can be administered parenterally, such as, in some embodiments, subcutaneously, intratumorally, intravenously. For example, in various embodiments the immune checkpoint inhibitor is administered at a dose of from about 1 mg/kg to about 5 mg/kg intravenously. The initial dose of the immune checkpoint inhibitor can be administered at least one week after the initial TLR9 agonist dose, for example in about weeks 2, 3 or 4. In some embodiments, the immunotherapy agent is administered from about 2 to about 6 times (e.g., about 4 times, preferably every three weeks).

In some embodiments, IMO-2125 is administered intratumorally to a metastatic melanoma patient previously found to be unresponsive or only partially responsive to PD-1 blockade therapy. For example, IMO-2125 is administered at a dose of from 4 to 32 mg per dose in weeks 1, 2, 3, 5, 8, and 11, with ipilimumab i.v. at 3 mg/kg. Ipilimumab can be administered every three weeks, beginning in week 2. Alternatively, pembrolizumab can be administered i.v. at 2 mg/kg every three weeks beginning on week 2.

The present methods in various embodiments allow for a robust anti-tumor immune response (which in some embodiments is a complete response), and which does not come at the expense of significant side effects, e.g. relative to side effects observed when one or more immunotherapies are used in the absence of the TLR9 agonist. Such side effects include commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease (among others).

Other aspects and embodiments will be apparent from the following detailed description.

BRIEF DESCRIPTION OF THE DRAWINGS

FIGS. 6A-H show a tumor study in the A20 model comparing intratumor and subcutaneous administration. FIGS. 6A-D show the study design and tumor kinetics while FIGS. 6E-H show the presence of tumor-infiltrating lymphocytes (TILs) and changes in gene expression of various checkpoint genes.

FIG. 8A shows number of lung tumor nodules in the various treatment groups and FIGS. 8B-E show images of tumors in the various treatment groups (pictures taken on Day 13 after tumor implantation).

FIGS. 10A-R show an evaluation of the antitumor activity of intratumoral IMO-2125 in combination with anti-PD-1 mAb in CT26 colon carcinoma tumor model.

FIG. 10A shows the study design. FIGS. 10B-I show the impact of the combination on tumor growth kinetics at treated and distal sites. FIG. 10J shows the impact of the combination on TILs (magnifications are shown). FIGS. 10K-R show checkpoint gene expression at treated and distal sites after treatment with the combination.

FIGS. 11A-N show an evaluation of the antitumor activity of intratumoral IMO-2125 in combination with anti-PD-1 mAb on treated tumors and systemic lung metastases in a B16 melanoma model. FIG. 11A shows the study design. FIGS. 11B-E show the impact of the combination on tumor growth kinetics at treated sites. FIGS. 11F-J show the combination's impact on lung metastases. FIGS. 11K-N show histopathology of metastatic lung tumors (Circle: Large tumor nodule, Arrow: Small tumor nodule, Inset figures: HE stained (×40), and Large figures: CD3 stained (×400)).

FIG. 13A shows the number of lung tumor nodules in each treatment group. FIG. 13B shows the change in tumor volume in each treatment group during the regimen.

FIGS. 15A-C show dendritic cell maturation results pre-dose and 24 hours post i.t. IMO-2125 injection for patient 003 (4 mg doses of IMO-2125).

FIGS. 15D-G show T-cell activation results in injected and distant tumors.

DETAILED DESCRIPTION

Figure 1:
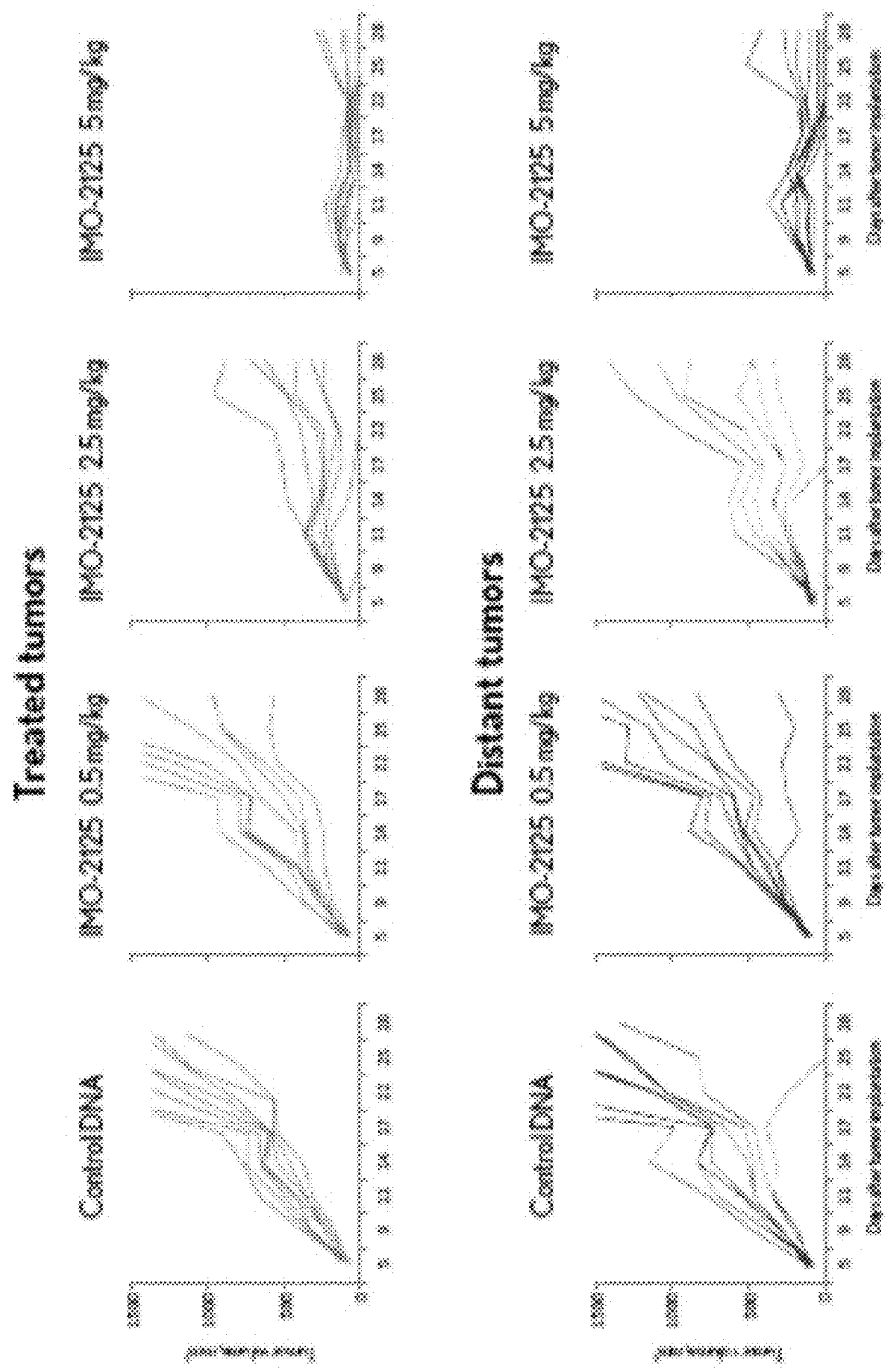
FIGS. 1A-H show tumor growth reduction in a CT26.CL25 tumor model with IMO-2125 monotherapy. Tumor volume for treated tumors and distant tumors is shown.

In various aspects, the present invention provides a method for treating a tumor, e.g. a metastatic tumor (including, without limitation, metastatic melanoma) comprising intratumorally administering an oligonucleotide TLR9 agonist (e.g., IMO-2125) to a cancer patient, in combination with immunotherapy with an immune checkpoint inhibitor therapy, such as a therapy targeting CTLA-4, PD-1/PD-L1/PD-L2, LAG3, TIM3, and/or IDO.

Exemplary immune checkpoint inhibitors include anti-PD-1, anti-PD-L1, anti-PD-L2, and anti-CTLA-4 agents. PD-1/PD-L1/PD-L2 antibodies inhibit the interaction between PD-1 and its ligands (PD-L1 and PD-L2) on tumor cells to promote immune-mediated tumor destruction. CTLA-4 antibodies block the inhibitory signals to T-cells transmitted by CTLA-4. While PD-1 antibodies and CTLA-4 antibodies have emerged as important therapeutic options for a variety of cancers, many patients fail to respond. For example, some melanoma patients show no response to anti-PD-1 treatment, or even progress, after 12 weeks of treatment. Further, immune checkpoint blockade is associated with various immune-related adverse events, which can affect various tissues and organs including the skin, the gastrointestinal tract, the kidneys, peripheral and central nervous system, liver, lymph nodes, eyes, pancreas, and the endocrine system. These immune-related adverse events (irAEs) can be severe, or even fatal, and may require discontinuation of therapy. Examples of common irAEs are hypophysitis, colitis, hepatitis, pneumonitis, rash, and rheumatic disease.

Expression of the various immune checkpoint molecules on cells of the immune system induces a complex series of events that determines whether an immune response will be effective to combat the tumor, or otherwise result in immune tolerance. For example, increased expression of PD-1 on dendritic cells (DCs) promotes apoptosis of activated DCs, a critical antigen presenting cell for anti-tumor immune responses. Park SJ, *Negative role of inducible PD-1 on survival of activated dendritic cells*, J. Leukocyte Biology 95(4):621-629 (2014). Further, expression of IDO, PD-L1, and CTLA-4 in the peripheral blood of melanoma patients and can be associated with advanced disease and negative outcomes, and are interconnected, suggesting that multiple immune checkpoints might require targeting to improve therapy in some cases. Chevolet I, et al., *Characterization of the in vivo immune networks of IDO, tryptophan metabolism, PD-L1, and CTLA-4 in circulating immune cells in melanoma*, Oncoimmunology 4(3) e982382-7 (2015).

The TLR9 agonist known as IMO-2125, which is described more fully herein, upon intratumoral injection induces global increases in expression of checkpoint genes, including IDO1 (5.3 fold), PDL1 (2.6 fold), PD1 (2.5 fold), IDO2 (5.9 fold), CEACAM1 (2.1 fold), OX40 (1.4 fold), TIM3 (2.9 fold), LAG3 (1.9 fold), CTLA4 (1.8 fold), and OX40L (1.5 fold). See FIG. 6B. By altering immune signaling in the tumor microenvironment, such changes in gene expression provide opportunities to improve responsiveness with checkpoint inhibitor therapy, and to achieve lasting anti-tumor immunity. Further, by targeting a single immune checkpoint molecule selected from the stronger inhibitory signals of PD-1 or CTLA-4, in connection with the robust activation of antigen presenting cells (e.g., DCs) and priming of T cells with IMO-2125, the invention provides the opportunity to balance anti-tumor responses with inhibitory signals, thereby also minimizing irAEs of checkpoint inhibitor therapy.

In various embodiments, the patient has a cancer that was previously unresponsive to, or had become resistant to, a checkpoint inhibitor therapy. For example, the cancer may be refractory or insufficiently responsive to an immunotherapy, such as anti-CTLA-4, anti-PD-1, or anti-PD-L1 and/or PD-L2 agent, including for example, one or more of ipilimumab, tremelimumab, pembrolizumab and nivolumab. In various embodiments, the cancer patient has progressed after or during treatment with an anti-CTLA-4, anti-PD-1, or anti-PD-L1 and/or PD-L2 agent, including for example, one or more of ipilimumab, tremelimumab, pembrolizumab and nivolumab (or agents related thereto) or shown no response to such treatment for at least about 12 weeks.

Other immune checkpoint inhibitors can be administered alone (e.g, in place of) or in combination with anti-CTLA4 or anti-PD-1/anti-PD-L1, such as an inhibitor of IDO (e.g., IDO-1 or IDO-2), LAG3, TIM3, among others. These and other immune checkpoint inhibitors are described in US 2016-0101128, which is hereby incorporated by reference in its entirety. For example, the patient may further receive a regimen of an IDO-1 inhibitor such as Epacadostat.

In various embodiments, the cancer is a primary cancer or a metastatic cancer. A primary cancer refers to cancer cells at an originating site that become clinically detectable, and may be a primary tumor. "Metastasis" refers to the spread of cancer from a primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant.

The cancer may have an origin from any tissue. The cancer may originate from skin, colon, breast, or prostate, and thus may be made up of cells that were originally skin, colon, breast, or prostate, respectively. The cancer may also be a hematological malignancy, which may be lymphoma. In various embodiments, the primary or metastatic cancer is lung cancer, kidney cancer, prostate cancer, cervical cancer, colorectal cancer, pancreatic cancer, ovarian cancer, urothelial cancer, gastric/GEJ cancer, head and neck cancer, glioblastoma, Merkel cell cancer, head and neck squamous cell carcinoma (HNSCC), non-small cell lung carcinoma (NSCLC), small cell lung cancer (SCLC), bladder cancer, prostate cancer (e.g. hormone-refractory) and hematologic malignancies.

In some embodiments, the cancer is progressive, locally advanced, or metastatic carcinoma. In some embodiments, the cancer is metastatic melanoma, and may be recurrent. In some embodiments, the metastatic melanoma is stage III or IV, and may be stage IVA, IVB, or IVC. The metastasis may be regional or distant.

IMO-2125 and related immunostimulatory oligonucleotides target TLR9, and act as TLR9 agonists to alter immune signaling in the tumor microenvironment, and induce anti-tumor T cell responses.

In accordance with various embodiments, the TLR9 agonist comprises at least two oligonucleotides linked together through their 3' ends, so as to have multiple accessible 5' ends. The linkage at the 3' ends of the component oligonucleotides is independent of the other oligonucleotide linkages and may be directly via 3' or 2' hydroxyl groups, or indirectly, via a non-nucleotide linker or a nucleoside, utilizing either the 2' or 3' hydroxyl positions of the nucleoside. Linkages may also employ a functionalized sugar or nucleobase of a 3' terminal nucleotide. Exemplary TLR9 agonists are described in U.S. Pat. Nos. 8,420,615, 7,566, 702, 7,498,425, 7,498,426, 7,405,285, 7,427,405, including Tables 1 and 2A-2D of each, the entire contents of which are hereby incorporated by reference in their entireties.

In various embodiments, the TLR agonist is selected from:

(SEQ ID NO: 1)
5'-TCTGACG$_1$TTCT-X-TCTTG$_1$CAGTCT-5'

(SEQ ID NO: 2)
5'-TCTGTCG$_1$TTCT-X-TCTTG$_1$CTGTCT-5'

(SEQ ID NO: 3)
5'-TCG$_1$TCG$_1$TTCTG-X-GTCTTG$_1$CTG$_1$CT-5'

(SEQ ID NO: 4)
5'-TCG$_1$AACG$_1$TTCG$_1$-X-G$_1$CTTG$_1$CAAG$_1$CT-5'

(SEQ ID NO: 5)
5'-CTGTCoG$_2$TTCTC-X-CTCTTG$_2$oCTGTC-5'

(SEQ ID NO: 6)
5'-CTGTCG$_2$TTCTCo-X-oCTCTTG$_2$CTGTC-5'

(SEQ ID NO: 7)
5'-TCG$_1$AACG$_1$TTCG$_1$-X-TCTTG$_2$CTGTCT-5'

(SEQ ID NO: 8)
5'-TCG$_1$AACG$_1$TTCG$_1$-Y-GACAG$_1$CTGTCT-5'

(SEQ ID NO: 9)
5'-CAGTCG$_2$TTCAG-X-GACTTG$_2$CTGAC-5'

(SEQ ID NO: 10)
5'-CAGTCG$_1$TTCAG-X-GACTTG$_1$CTGAC-5'

(SEQ ID NO: 11)
5'-TCG$_1$AACG$_1$TTCoG̲-Z-G̲oCTTG$_1$CAAG$_1$CT-5'

(SEQ ID NO: 12)
5'-TCG$_1$AACG$_1$TTCG$_1$-Y$_2$-TCTTG$_1$CTGTCTTG$_1$CT-5'

(SEQ ID NO: 13)
5'-TCG$_1$AACG$_1$TTCG$_1$-Y$_2$-TCTTG$_1$CTGU̲CT-5'

(SEQ ID NO: 14)
5'-TCG$_1$AACG$_1$ToTCoG̲-m-G̲oCToTG$_1$CAAG$_1$CT-5'

-continued (SEQ ID NO: 15)
5'-TCG₁AACG₁TTCoG-Y₃-GACTTG₂CTGAC-5'

(SEQ ID NO: 16)
5'-TCG₁AACG₁TTCG₁-Y₄-TGTTG₁CTGTCTTG₁CT-5'

(SEQ ID NO: 17)
5'-TCG₂TCG₂TTU₁Y-M-YU₁TTG₂CTG₂CT-5'

(SEQ ID NO: 18)
5'-CAGTCG₂TTCAG-Y₃-TCTTG₁CTGTCT-5'

(SEQ ID NO: 19)
5'-TCG₁TACG₁TACG₁-X-G₁CATG₁CATG₁CT-5'

(SEQ ID NO: 20)
5'-TCG₁AACG₁TTCG-Z-GCTTG₁CAAG₁CT-5'

(SEQ ID NO: 21)
5'-TCG₁AACG₁TTCoG-Y₃-CTTG₂CTGACTTG₁CT-5'

(SEQ ID NO: 22)
5'-TCG₁AACG₁oTTCG₁-X₂-G₁CTToG₁CAAG₁CT-5'

(SEQ ID NO: 23)
5'-TCG₁AACG₁TTCG₁-Y₄-CATTG₁CTGTCTTG₁CT-5'

(SEQ ID NO: 24)
5'-TCG₁AACG₁TTCG₁-m-G₁CTTG₁CAAG₁CT-5'

(SEQ ID NO: 25)
5'-TCoG₁oAACoG₁TTCoG₁o-X₂-oG₁oCTTG₁oCAAoG₁oCT-5'

(SEQ ID NO: 26)
5'-ToCG₁oAACoG₁TTCoG₁o-X₂-oG₁oCTTG₁oCAAoG₁CoT-5'

(SEQ ID NO: 27)
5'-TCoG₁oAACoG₁TTCoG₁o-m-oG₁oCTTG₁oCAAoG₁oCT-5'

(SEQ ID NO: 28)
5'-TCoG₂oAACoG₂TTCoG₂o-X₂-oG₂oCTTG₂oCAAoG₂oCT-5'

(SEQ ID NO: 29)
5'-TCoG₁oAACoG₁TTCoGo-Z-oGoCTTG₁oCAAoG₁oCT-5'
and (SEQ ID NO: 30)
5'-ToCG₁oAACoG₁TTCoGo-Z-oGoCTTG₁oCAAoG₁CoT-5', where $G_1$ is 2'-deoxy-7-deazaguanosine; $G_2$ is 2'-deoxy-arabinoguanosine; G, C, or U are 2'-O-methylribonucleotides; $U_1$ is 2'-deoxy-U; o is a phosphodiester linkage; X is a glycerol linker; $X_2$ is a isobutanetriol linker, Y is C3-linker; m is cis,trans-1,3,5-cyclohexanetriol linker; $Y_2$ is 1,3-propanediol linker; $Y_3$ is 1,4-butanediol linker; $Y_4$ is 1,5-pentandiol linker; Z is 1,3,5-pentanetriol linker; and M is cis,cis-1,3,5-cyclohexanetriol linker.

In various embodiments, the TLR9 agonist is selected from 5'-TCG₁AACG₁TTCG₁-X-G₁CTTG₁CAAG₁CT-5' (SEQ ID NO:4), 5'-CTGTCoG₂TTCTC-X-CTCTTG₂oCTGTC-5' (SEQ ID NO:5), 5'-CTGTCG₂TTCTCo-X-oCTCTTG₂CTGTC-5' (SEQ ID NO:6), 5'-TCG₁AACG₁TTCG₁-Y-TCTTG₂CTGTCT-5' (SEQ ID NO:7), and 5'-TCGAACG₁TTCG₁-Y-GACAG₁CTGTCT-5' (SEQ ID NO:8), wherein X is a glycerol linker, Y is a C3-linker, $G_1$ is 2'-deoxy-7-deazaguanosine, $G_2$ is arabinoguanosine, and o is a phosphodiester linkage.

In various embodiments, the TLR9 agonist is 5'-TCG₁AACG₁TTCG₁-X-G₁CTTG₁CAAG₁CT-5' (SEQ ID NO:4), wherein X is a glycerol linker and $G_1$ is 2'-deoxy-7-deazaguanosine, otherwise known as IMO-2125.

Alternative TLR9 agonists are immune stimulatory oligonucleotides disclosed in U.S. Pat. No. 8,871,732, which is hereby incorporated by reference in its entirety. Such agonists comprise a palindromic sequence of at least 8 nucleotides and at least one CG dinucleotide.

In accordance with embodiments of the invention, the immunostimulatory oligonucleotide (e.g., IMO-2125) is administered intratumorally. In some embodiments, the intratumoral administration is in a primary or secondary tumor (e.g., metastatic melanoma lesion). Intratumoral administration alters immune signaling in the tumor microenvironment, priming the immune system for an effective anti-tumor response, while inducing changes that are compatible with more effective checkpoint inhibitor therapy.

Illustrative dosage forms suitable for intratumoral administration include solutions, suspensions, dispersions, emulsions, and the like. The TLR9 agonist may be provided in the form of sterile solid compositions (e.g. lyophilized composition), which can be dissolved or suspended in sterile injectable medium immediately before use. They may contain, for example, suspending or dispersing agents known in the art.

In various embodiments, the TLR9 agonist is IMO-2125 and is administered intratumorally at from about 4 mg to about 64 mg per dose, or in some embodiments from about 8 mg to about 64 mg per dose, or from about 12 mg to about 64 mg per dose, or from about 16 mg to about 64 mg per dose, or from about 20 mg to about 64 mg per dose. In some embodiments, IMO-2125 is administered at from about 20 mg to about 48 mg per dose, or about 20 mg to about 40 mg per dose. For example, in various embodiments, IMO-2125 is administered at about 4 mg, or about 8 mg, or about 12 mg, or about 16 mg, or about 20 mg, or about 24 mg, or about 28 mg, or about 32 mg, or about 36 mg, or about 40 mg, or about 44 mg, or about 48 mg, or about 52 mg, or about 56 mg, or about 60 mg, or about 64 mg per dose, e.g. intratumorally.

In various embodiments, about 3 to about 12 doses of the TLR9 agonist (e.g. IMO-2125) are administered (e.g. about 3 doses, or about 4 doses, or about 5 doses, or about 6 doses, or about 7 doses, or about 8 doses, or about 9 doses, or about 10 doses, or about 11 doses, or about 12 doses). In various embodiments, about 4 to about 8 doses are administered over 10 to 12 weeks. In some embodiments, about 6 doses are administered over 10 to 12 weeks. In some embodiments, therapy is initiated with 3 to 5 weekly doses of IMO-2125, optionally followed by 3 to 8 maintenance doses, which are administered about every three weeks. In some embodiments, an IMO-2125 dose is administered in weeks 1, 2, 3, 5, 8, and 11. The IMO-2125 doses may be administered in the same or different lesions.

During the regimen of IMO-2125 (or other TLR9 agonist), one or more checkpoint inhibitor therapies are administered to take advantage of the changes in immune signaling. The one or more checkpoint inhibitors can be administered parenterally, including intravenously, intratumorally, or subcutaneously, among other methods. In some embodiments, the patient receives an anti-CTLA-4 agent. For example, the anti-CTLA-4 agent may be an antibody that targets CTLA-4, for instance an antagonistic antibody. In various embodiments, the anti-CTLA-4 is ipilimumab (e.g. YERVOY, BMS-734016, MDX-010, MDX-101). In various embodiments, the anti-CTLA-4 is tremelimumab (e.g. CP-675,206, MEDIMMUNE). In other embodiments, the immunotherapy agent is an anti-PD-1 agent. For example, the anti-PD-1 agent may be an antibody that targets the PD-1, for instance, inhibiting the interaction between PD-1 and PD-L1 (and/or PD-L2). In various embodiments, the anti-PD-1 agent is nivolumab (ONO-4538/BMS-936558, MDX1106 or OPDIVO). In various embodiments, the anti-PD-1 agent is pembrolizumab (KEYTRUDA or MK-3475). In various embodiments, the anti-PD-1 agent is pidilizumab (CT-011 or MEDIVATION).

In some embodiments, the present immunotherapy agent is an anti-PD-L1 and/or PD-L2 agent. For example, in various embodiments, the anti-PD-L1 and/or PD-L2 agent is an antibody that targets PD-L1 and/or PD-L2, for instance, inhibiting the interaction between PD-1 and PD-L1 and/or PD-L2. In various embodiments, the anti-PD-L1 and/or PD-L2 agent is atezolizumab (TECENTRIQ, ROCHE) BMS 936559 (BRISTOL MYERS SQUIBB), or MPDL328OA (ROCHE).

In various embodiments, the anti-CTLA-4, anti-PD-1, or anti-PD-L1 and/or PD-L2 agent (e.g. YERVOY, OPDIVO, or KEYTRUDA, or comparable agents thereto) is administered at a dose of about 1 mg/kg, or about 2 mg/kg, or about 3 mg/kg, or about 4 mg/kg, or about 5 mg/kg, e.g. intravenously. For example, in some embodiments, the dose of an anti-CTLA-4 agent, e.g. YERVOY, is about 3 mg/kg. For example, in some embodiments, the dose of an anti-PD-1 agent, e.g. OPDIVO, is about 3 mg/kg. For example, in some embodiments, the dose of an anti-PD-1 agent, e.g. KEYTRUDA, is about 2 mg/kg. In various embodiments, the initial dose of the anti-CTLA-4, anti-PD-1, or anti-PD-L1 and/or PD-L2 agent (e.g. YERVOY, OPDIVO, or KEYTRUDA, or comparable agents thereto) is administered at least one week after the initial TLR9 agonist dose, for example in about weeks 2, 3 or 4.

In some embodiments, the immunotherapy agent is anti-CTLA-4 (e.g. YERVOY), anti-PD-1 (e.g. OPDIVO or KEYTRUDA), or anti-PD-L1 and/or anti-PD-L2 agent, which is administered from about 2 to about 6 times (e.g. about 2 times, or about 3 times, or about 4 times, or about 5 times, or about 6 times). In some embodiments, the immunotherapy agent, e.g. anti-CTLA-4 (e.g. YERVOY), anti-PD-1 (e.g. OPDIVO or KEYTRUDA), or anti-PD-L1 and/or PD-L2 agent is administered about 4 times.

In some embodiments, the immunotherapy agent is an anti-CTLA-4 agent such as YERVOY and is dosed at 3 mg/kg i.v. over about 90 minutes about every 3 weeks. In some embodiments, the immunotherapy agent is an anti-PD-1 agent such as OPDIVO and is dosed at about 3 mg/kg i.v. over about 60 minutes about every 2 weeks. In some embodiments, the immunotherapy agent is an anti-PD-1 agent such as KEYTRUDA and is dosed at about 2 mg/kg i.v. over about 30 minutes about every 3 weeks.

In some embodiments, maintenance doses of the TLR9 agonist (e.g. IMO-2125), along with dosing of anti-CTLA-4, anti-PD-1, or anti-PD-L1 and/or PD-L2 agent (e.g. YERVOY, OPDIVO, or KEYTRUDA, or comparable agents thereto) are administered about every 3 weeks.

In various embodiments, the present immunostimulatory oligonucleotides allow for a dose reduction of the immunotherapy to about 10%, or about 20%, or about 30%, or about 40%, or about 50%, or about 60%, or about 70%, or about 80%, or about 90%, or about 100% of a monotherapy dose. For example, in some embodiments, an immunotherapy dose is about 0.1 mg/kg, or about 0.3 mg/kg, or about 0.5 mg/kg, or about 0.7 mg/kg, or about 1 mg/kg, or about 1.5 mg/kg, or about 2 mg/kg, or about 2.5 mg/kg, or about 3 mg/kg.

In some embodiments, IMO-2125 is administered intratumorally to a metastatic melanoma patient previously found to be unresponsive or only partially responsive to PD-1 blockade therapy. IMO-2125 is administered at a dose of from 4 to 32 mg per dose (e.g., about 16 mg, about 20 mg, about 24 mg, about 28 mg, or about 32 mg) in weeks 1, 2, 3, 5, 8, and 11, with ipilimumab i.v. at 3 mg/kg. Ipilimumab can be administered every three weeks, beginning in week 2 (e.g., weeks 2, 5, 8, and 11). Alternatively, pembrolizumab can be administered i.v. at 2 mg/kg every three weeks beginning on week 2 (e.g., weeks 2, 5, 8, and 11).

In some embodiments, the patient further receives a regimen of Epacadostat (an IDO-1 inhibitor), which may be administered at from 25 mg to 300 mg orally, about twice daily. The regimen may be administered for about 5 day cycles. The first dose of Epacadostat may be administered starting at about one week following the initial IMO-2125 (or other TLR9 agonist) intratumoral injection.

In various embodiments, without wishing to be bound by theory, the invention provides for a more balanced immune response in a cancer patient, including cancer patients with advanced, metastatic disease. The combination therapy described herein can eliminate or reduce deficiencies that are observed in the respective monotherapies. For example, various patients are refractory to immunotherapies, or such monotherapies are hampered by extensive side effect profiles. Further as the field is moving to combinations of immunotherapies (e.g. YERVOY and OPDIVO), such side effects are likely to be more problematic.

In various embodiments, the combination therapy allows for activation and/or maturation of dendritic cells, e.g. plasmacytoid dendritic cells, and modulates the tumor microenvironment (TME) in both treated and distant tumors. For example, in various embodiments, the combination therapy provides for improvements in the amount or quality of TILs and/or CD8$^+$ T cells to promote anti-tumor activities. For example, primed T cells are observed to invade both the proximal and distal tumors. Such primed T cells are suited for tumor invasion, particularly at distal sites (e.g. secondary tumors), and, without wishing to be bound by theory, encounter a tumor environment that has reduced tolerance mechanisms in place. In various embodiments, the combination therapy provides for stimulation of interferons (e.g. IFN-α) and various Th1 type cytokines (e.g. IFN-γ, IL-2, IL-12, and TNF-β).

The invention provides, in various embodiments, methods for treating cancers, including metastatic cancers, in which the overall host immune milieu is reengineered away from tumor tolerance. For example, a local TME is created that both disrupts pathways of immune tolerance and suppression and allow for tumor regression. The present methods provide in some embodiments, a TME capable of propagating a robust immune response.

In various embodiments, a cancer patient's DCs are immature and unable to take up, process, or present antigens. These DCs may also be inhibited from migrating to regional lymph nodes or may induce tolerance, especially when presenting self-antigens. The cancer patient's tumor site may also be infiltrated with regulatory T cells that are able to mediate suppression of antigen-primed T cells. The helper CD4 T cell response may also be skewed toward a Th2 phenotype, which inhibits the initiation of Th1 T cells and effective cellular immunity. The tumor cells may express aberrant MHC class I molecules or β2-microglobulin, resulting in inadequate antigen presentation and, thus, inefficient recognition of tumors by effector T cells. Finally, tumor cells and the surrounding stroma may release a number of suppressive cytokines, such as IL-6, IL-10, and TGF-β. This creates an environment that is not conducive to local immunity, which allows tumor cells to escape. In various embodiments, the present methods allow for an environment that is conducive to local immunity against tumors, e.g., without limitation, maturation of DCs and/or reduction of regulatory T cells and Th2 CD4 T cells.

In some embodiments, the combination therapy according to the invention alters the balance of immune cells in favor of immune attack of a tumor. For instance, in some embodiments, the present methods shift the ratio of immune cells at a site of clinical importance, e.g. at the site of agent administration or a distal site, in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), B cells, dendritic cells, or subsets thereof) and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present methods increase a ratio of effector T cells to regulatory T cells. In various embodiments, this altered balance of immune cells is affected locally/proximally and/or systemically/distally. In various embodiments, this altered balance of immune cells is affected in the TME.

Further, in various embodiments, the present methods allow for a robust anti-tumor immune response that does not come at the expense of significant side effects (e.g., irAEs), e.g. relative to side effects observed when one or more immunotherapies are used in the absence of the TLR9 agonist.

For example, the combination therapy reduces one or more side effects of an immunotherapy, e.g. an anti-CTLA-4, anti-PD-1, or anti-PD-L1 and/or PD-L2 agent, including for example, one or more of YERVOY, OPDIVO, and KEYTRUDA or agents related thereto. Such side effects include: fatigue, cough, nausea, loss of appetite, skin rash, itching pruritus, rash, and colitis. In some embodiments, the side effects are intestinal problems (e.g. colitis) that can cause perforations in the intestines. Signs and symptoms of the colitis may include: diarrhea or more bowel movements than usual; blood in the stools or dark, tarry, sticky stools; and abdominal pain or tenderness. In some embodiments, the side effects are liver problems (e.g. hepatitis) that can lead to liver failure. Signs and symptoms of hepatitis may include: yellowing of skin or the whites of the eyes; dark urine; nausea or vomiting; pain on the right side of the stomach; and bleeding or bruising more easily than normal. In some embodiments, the side effects are skin problems that can lead to severe skin reactions. Signs and symptoms of severe skin reactions may include: skin rash with or without itching; sores in the mouth; and the skin blisters and/or peels. In some embodiments, the side effects are nerve problems that can lead to paralysis. Symptoms of nerve problems may include: unusual weakness of legs, arms, or face; and numbness or tingling in hands or feet. In some embodiments, the side effects are hormone gland problems (e.g. pituitary, adrenal, and thyroid glands). Signs and symptoms include: persistent or unusual headaches; unusual sluggishness; feeling cold all the time; weight gain; changes in mood or behavior such as decreased sex drive, irritability, or forgetfulness; and dizziness or fainting. In some embodiments, the side effects are ocular problems. Symptoms may include: blurry vision, double vision, or other vision problems; and eye pain or redness.

In some embodiments, patients experience fewer incidences of colitis, crohn's disease, or other GI involved irAE in accordance with the present invention.

In some embodiments, the patient achieves longer progression-free interval or longer survival (e.g., as compared to monotherapy), or in some embodiments, achieves remission or complete response. A complete response refers to the disappearance of all signs of cancer in response to treatment.

This invention is further illustrated by the following non-limiting examples.

EXAMPLES

Example 1: Anti-Tumor Effects of Immunostimulatory Oligonucleotides (IMO-2125)

Figure 2:
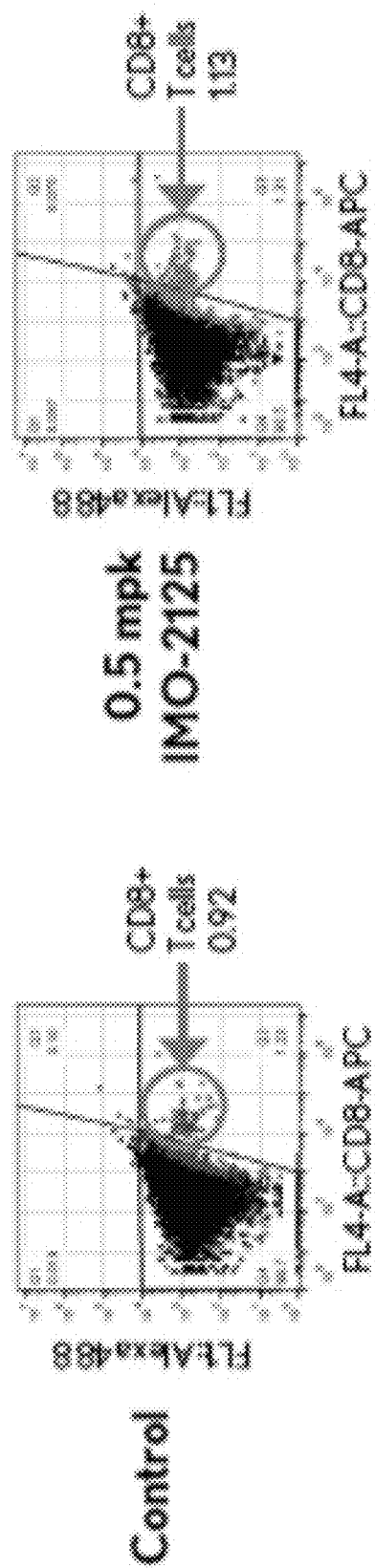
FIGS. 2A-F show tumor infiltrating lymphocytes in tumor nodules from Day 28 of the experiment shown in FIG. 1A-H. Magnification is ×400.
FIGS. 2G-H show FACS data that shows $CD8^+$ T cells tumor infiltration with IMO-2125 monotherapy (0.5 mg/kg).

Immunomers were synthesized as is known in the art (see, e.g., International Patent Publication No. WO 2016/057898, the entire contents of which, inclusive of Example 1 and FIGS. 1 and 2 therein, are hereby incorporated by reference).

BALB/c mice (n=8 per group) were implanted s.c. with $2 \times 10^6$ CT26.WT cells on right flank (Tumor 1) and $2 \times 10^6$ CT26.CL25 cells on the left flank (Tumor 2). Treatment was initiated on Day 5 when tumor volume on right flank reached 50 to 150 mm$^3$.

Test compound was administered by intratumoral (i.t.) injection (100 µl) on right side tumor nodules (Tumor 1) only at Days 5, 8, 11 and 14. Tumor nodules were collected at Day 28. The text compounds were Control DNA, IMO-2125: 0.5 mg/kg, IMO-2125: 2.5 mg/kg, and IMO-2125: 5 mg/kg. As shown in FIGS. 1A-H, intratumoral IMO-2125 treatment led to dose-dependent decreases in tumor volume in both treated and distant tumors. FIGS. 2A-H show tumor nodules collected on Day 28 after tumor implantation. Immunohistochemical staining for CD3$^+$ T lymphocyte surface marker. CD3$^+$ cells stained brown color. While few CD3$^+$ cells presented inside tumor tissue bordering normal tissue from placebo-injected mice, a large number of CD3$^+$ cells presented in the tumor tissue from mice treated with IMO-2125, 2.5 mg/kg. Results are shown in FIGS. 2A-F, which demonstrates inter alia, antitumor activity was associated with induction of tumor infiltrating lymphocytes (TILs). FIGS. 2G-H show that intratumoral IMO-2125 treatment increased infiltration of CD8$^+$ T cells in tumors.

Figure 3:
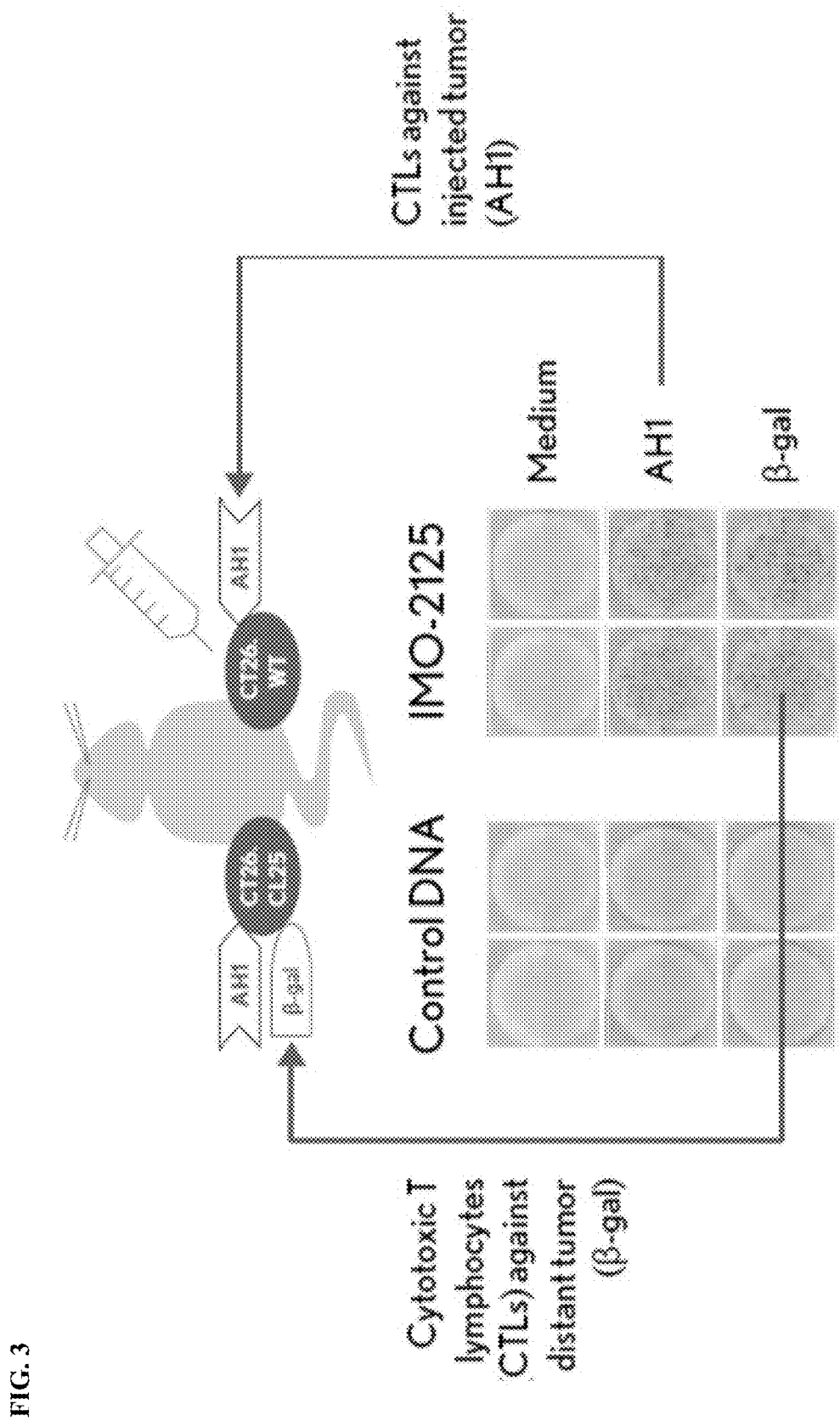
FIG. 3 shows assays to demonstrate specific cytotoxic T cell responses to tumor antigens.
Figure 4:
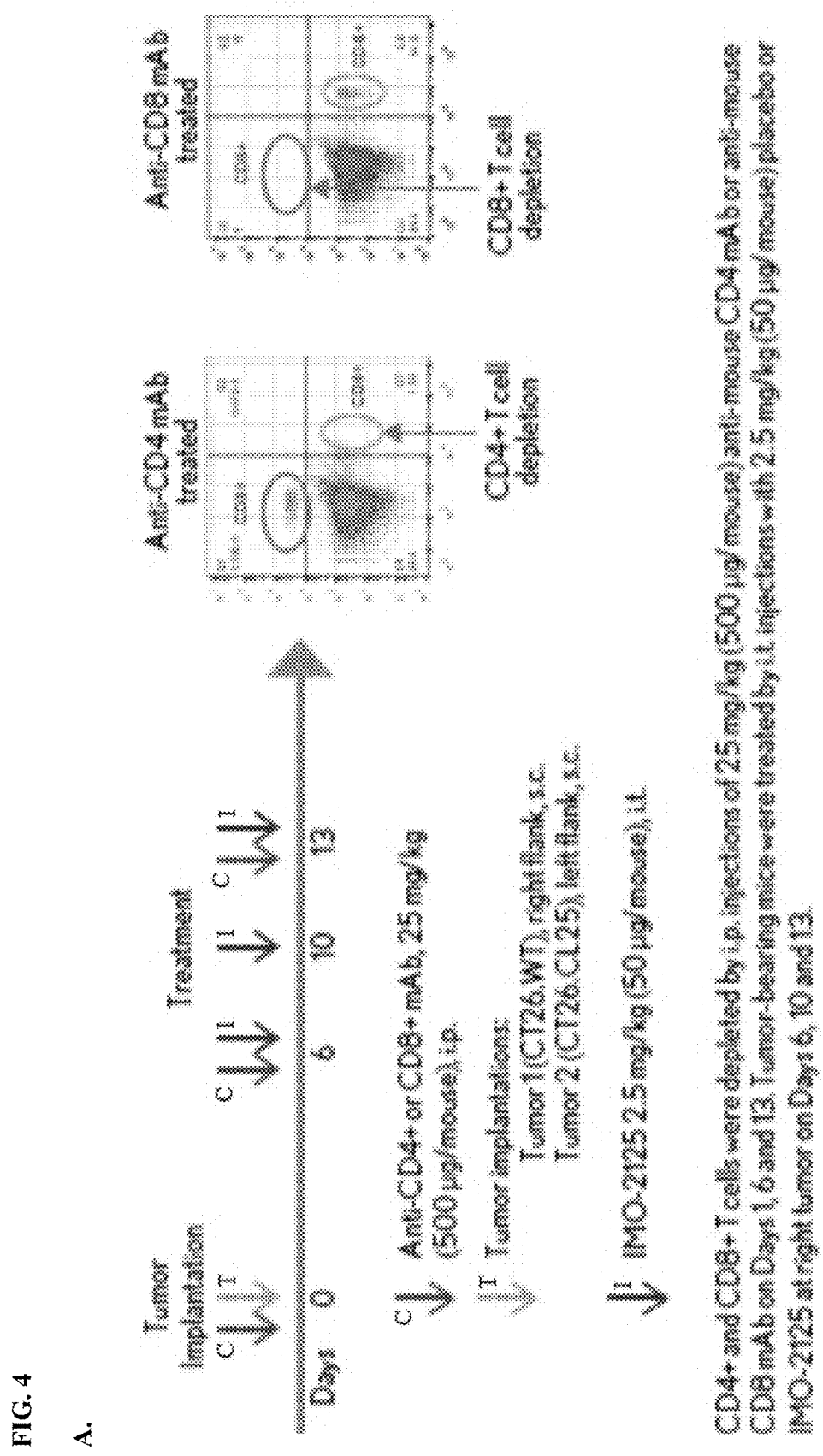
FIGS. 4A-C show a study design to evaluate the relationship of intratumoral IMO-2125 antitumor activity and infiltrating $CD4^+$ and $CD8^+$ T cells.
FIGS. 4D-E show the impact of $CD4^+$ and $CD8^+$ T cell depletion in treated and distal tumors.
Figure 4:
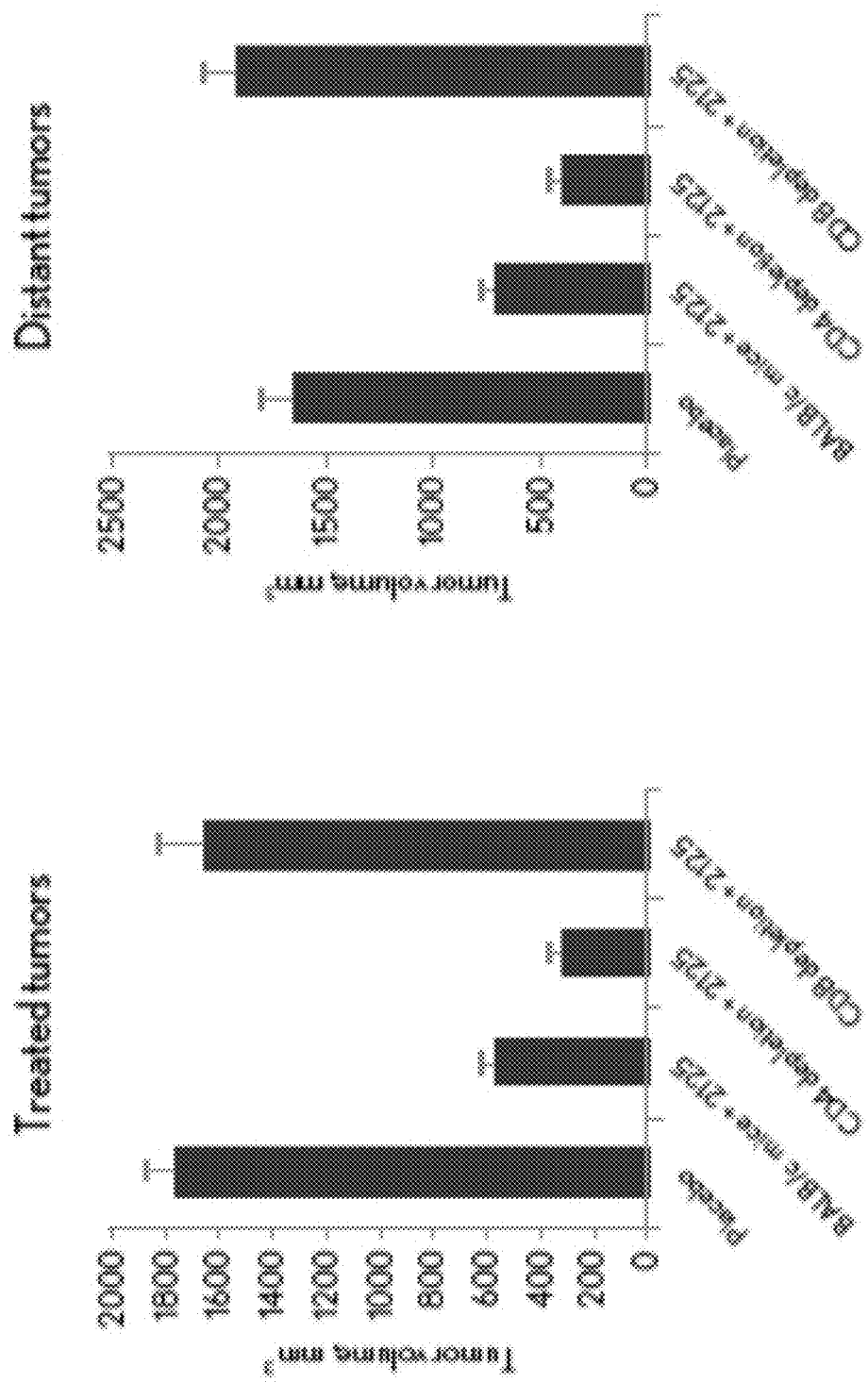

Further, T cells from spleens of placebo—and IMO-2125 (2.5 mg/kg)—treated tumor-bearing mice (n=3) were collected on Day 28. IFN-secreting ELISPOT was used for determining T cells specifically against tumor internal antigen AH1 presented in both CT26.WT and CT26.CL25 and β-gal presented only in CT26.CL25. FIG. 3 shows that intratumoral IMO-2125 treatment elicited specific cytotoxic T cell responses to tumor antigens. In FIGS. 4A-E, the key role of CD8$^+$ T cells in treated and distal tumors is demonstrated.

Figure 5:
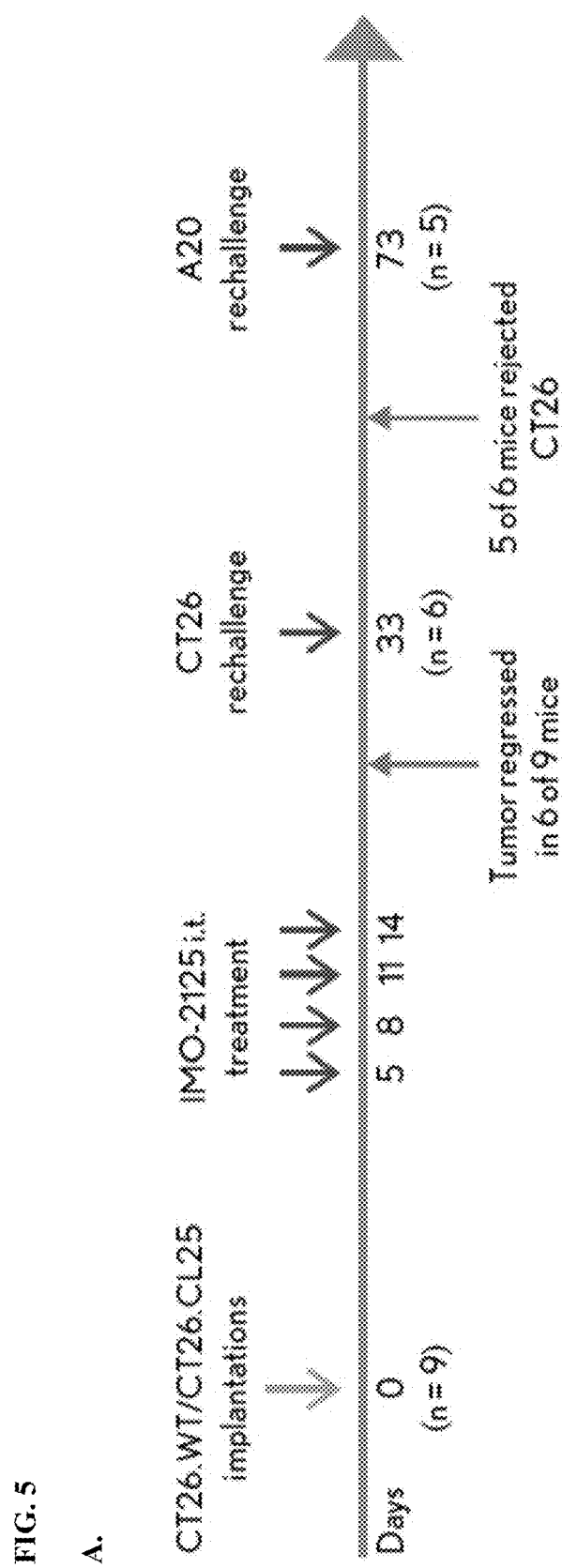
FIG. 5A shows a study design to evaluate the duration and specificity of the antitumor response induced by intratumoral IMO-2125 treatment.
FIG. 5B-C show the tumor growth of mice rechallenged with CT26 or A20 and intratumoral IMO-2125.
Figure 5:
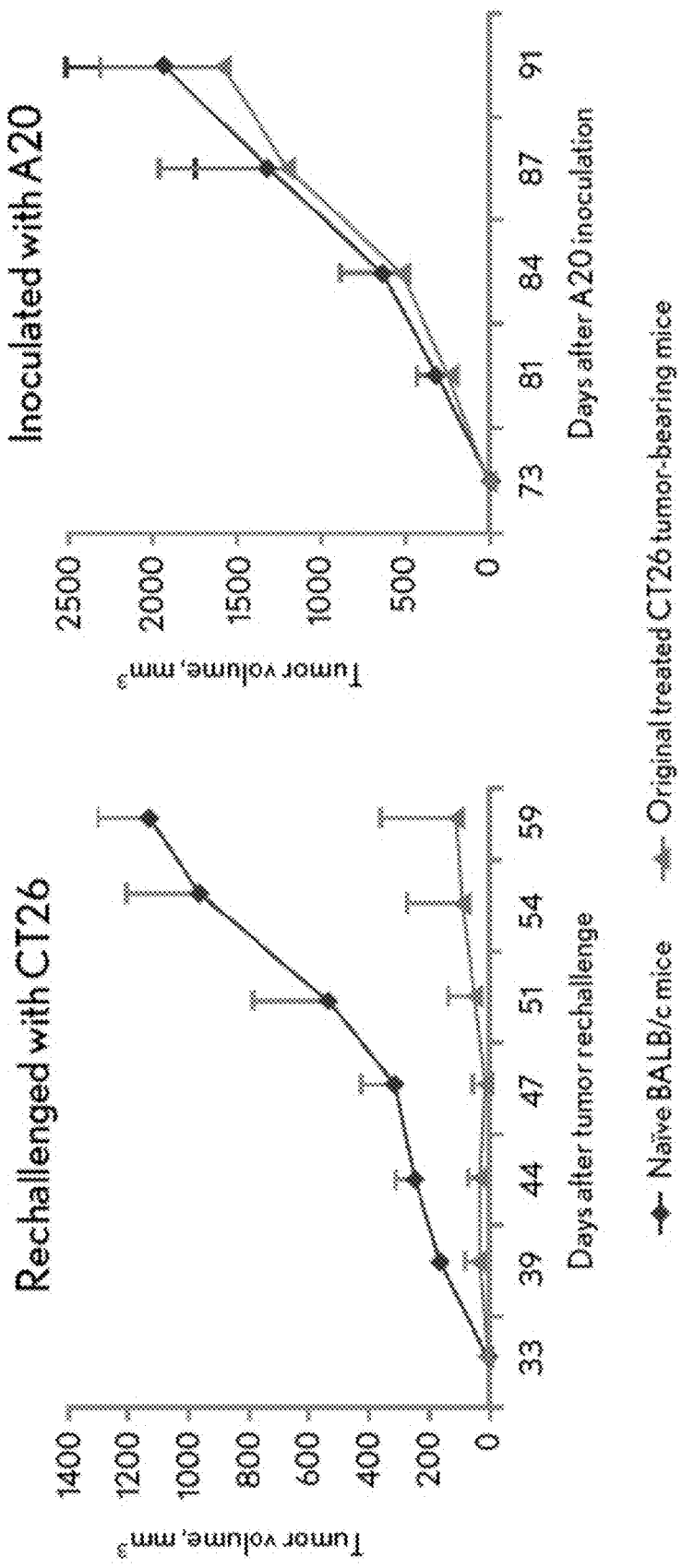

FIGS. 5A-C show a study demonstrating intratumoral IMO-2125 induced durable and tumor-specific immune memory. Six tumor-bearing mice (6 of 9) whose tumors completely or partially regressed (<150 mm3) after IMO-2125 (5 mg/kg, i.t.) treatments and 8 naïve BALB/c mice (n=8) were rechallenged on Day 33 with 1×106 CT26 cells by s.c. injection at abdominal right and left flank. Naïve BALB/c mice inoculated same way were used as tumor growth control. The mice that rejected CT26 tumor cell rechallenge (5 of 6) were then inoculated on Day 73 with 106 syngeneic, non-organ-related B cell lymphoma A20 cells by s.c. inoculation at the upper back area. See the plan of FIG. 5A. Results are shown in FIGS. 5B-C.

Figure 7:
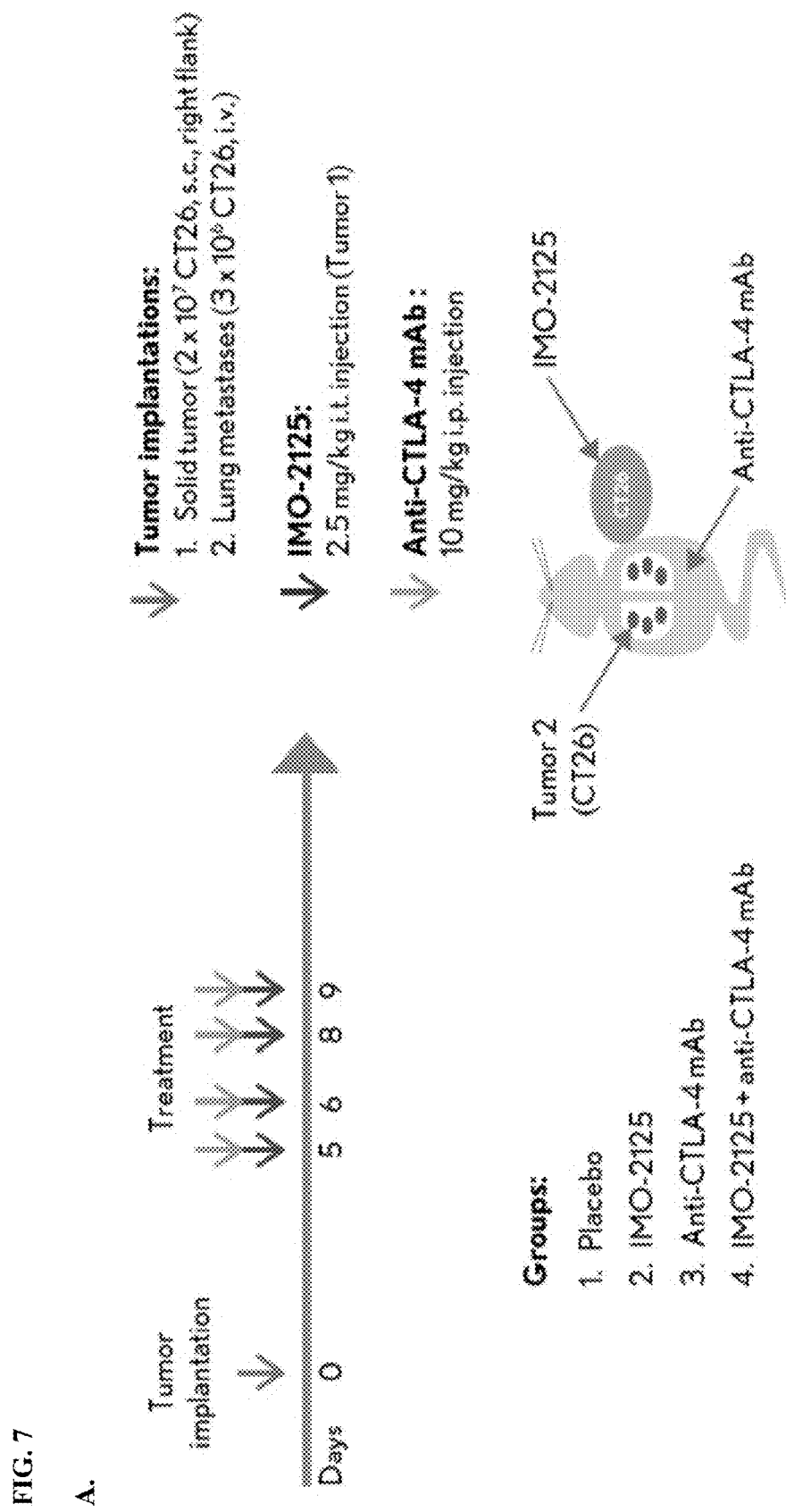
FIG. 7A shows a study design to evaluate the antitumor activity of intratumoral IMO-2125 in combination with anti-CTLA-4 mAb on treated tumors and systemic lung metastases.
FIGS. 7B-E show the anti-tumor effects of intratumoral IMO-2125 and anti-CTLA-4 mAb alone or in combination.
Figure 7:
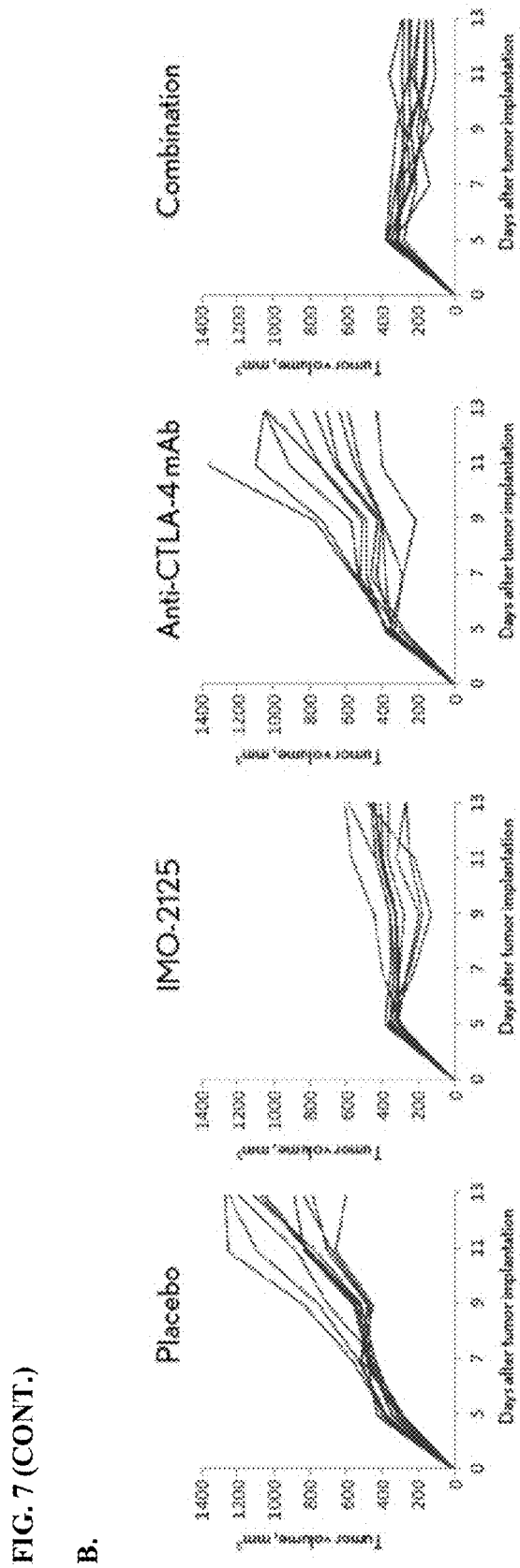
Figure 8:
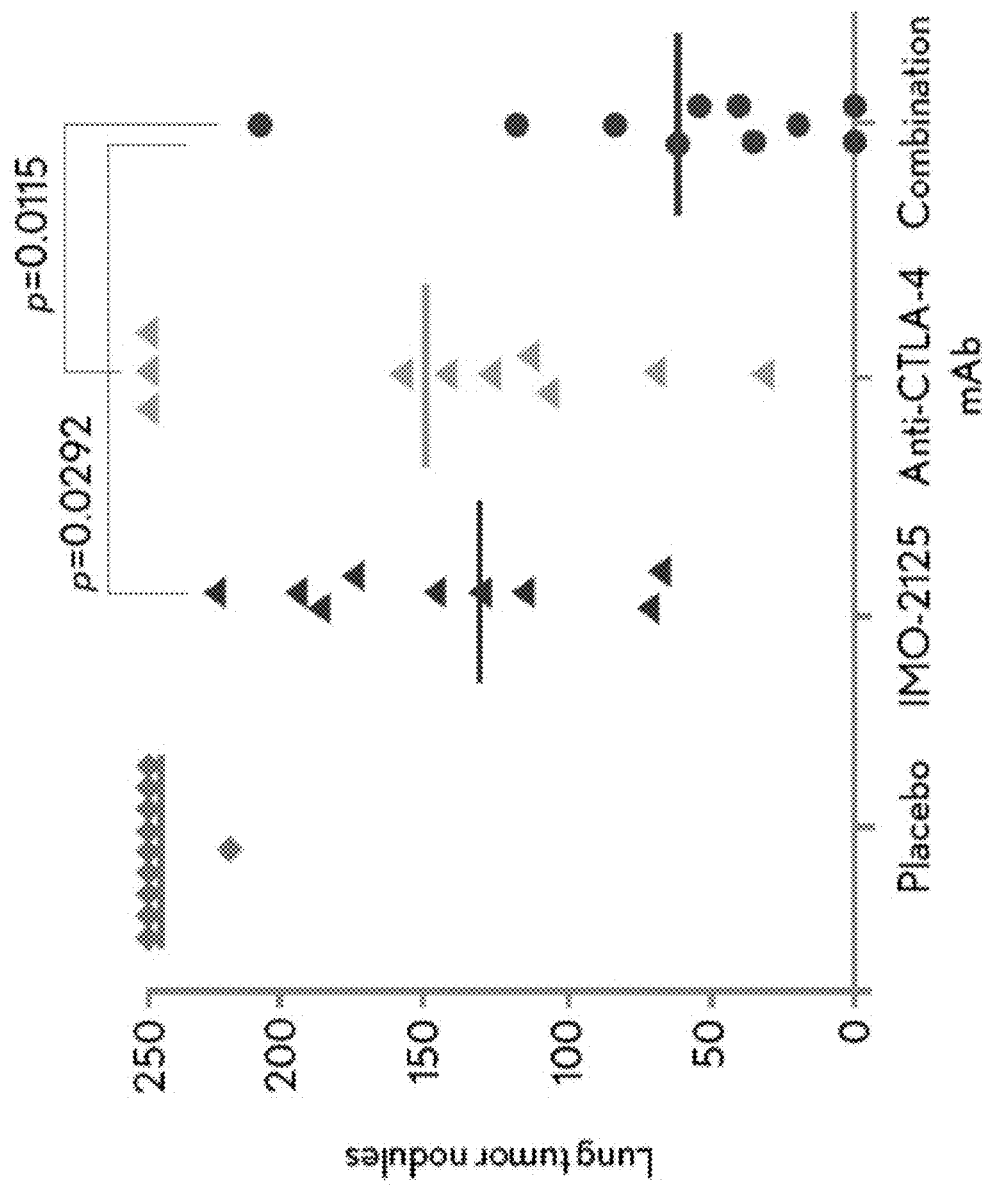
FIGS. 8A-E show anti-tumor activities of IMO-2125 and anti-CTLA-4 mAb alone or in combination on systemic lung metastasis.
Figure 8:
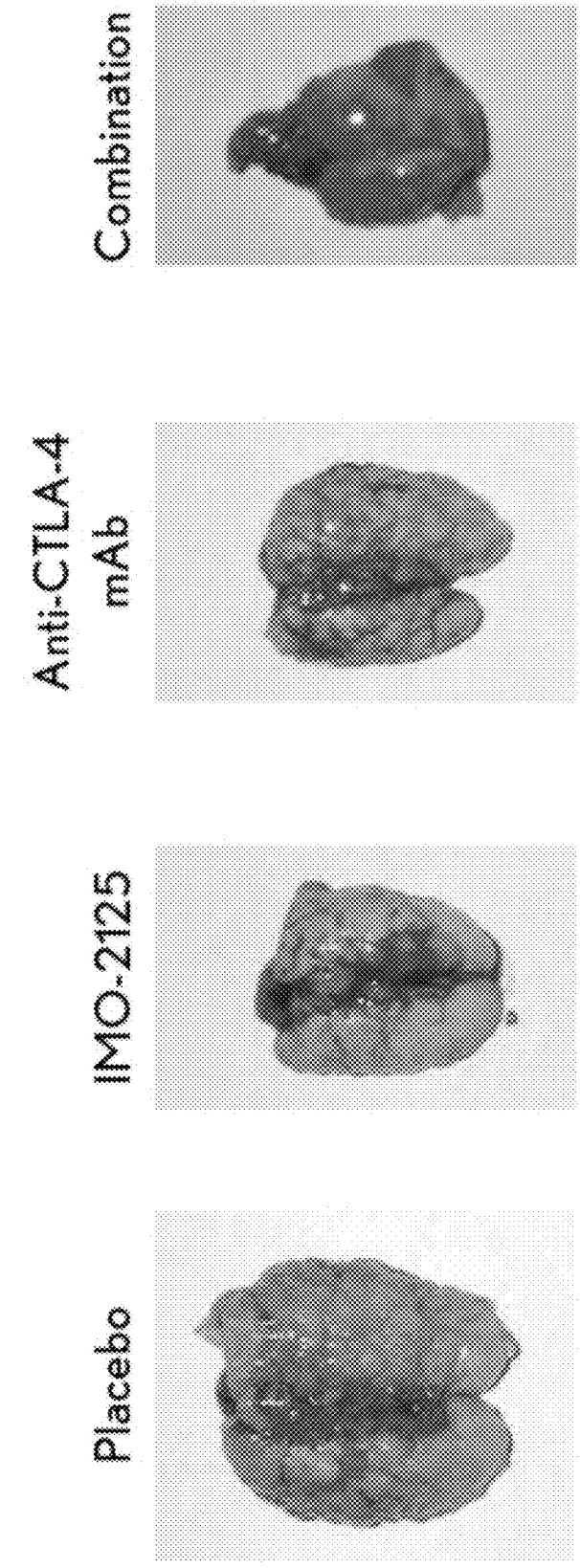
Figure 9:
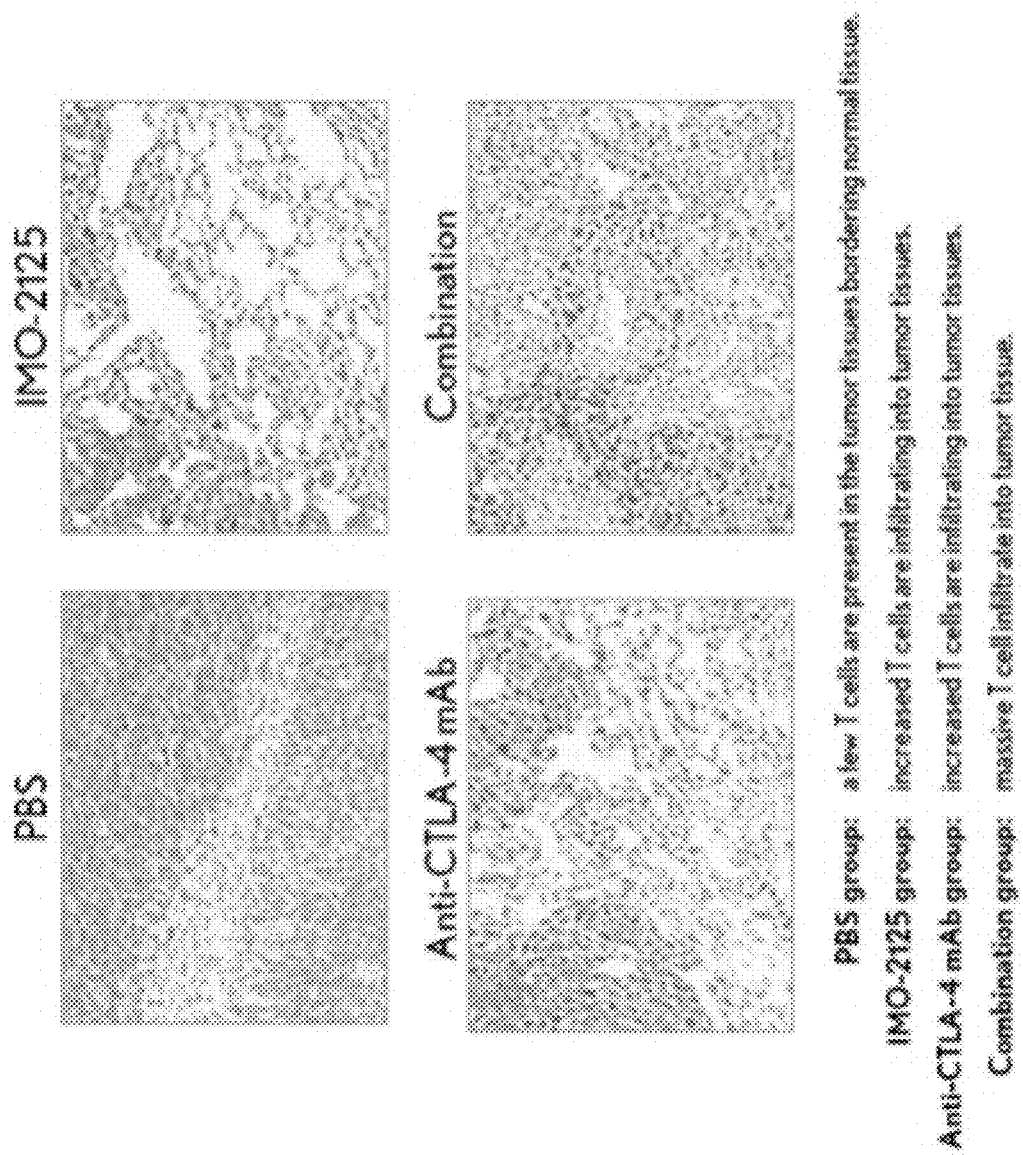
FIGS. 9A-D show TILs in metastatic nodules in the various treatment groups (CD3 IHC stain×400).

In FIGS. 6A-H, a study comparing intratumoral IMO-2125 is more effective than systemic (s.c.) treatment as demonstrated by antitumor activity in an A20 lymphoma model. BALB/c mice (n=10) were implanted s.c. with $3 \times 10^6$ A20 cells on the right and left flank. Treatment was initiated on day 8 with intratumoral injection in the left flank with 2.5 mg/kg IMO-2125. IMO-2125 was given on days 8, 10, 12, and 14. Samples from placebo (PBS) control and IMO-2125 treated tumor-bearing mice were collected on day 21 after tumor implantation. FIGS. 6A-D show the study design and tumor kinetics. In FIGS. 6B-D, the tumor kinetics of subcutaneous administration is slightly better than control while intratumoral administration significantly slows tumor growth. FIGS. 6E-H show the presence of TILs and changes in gene expression of various checkpoint genes. Importantly, IMO-2125 increased tumoral TILs and modulated tumor checkpoint expression thereby sensitizing the TME for combination with one or more checkpoint inhibitors Example 2: Anti-Tumor Effects of Combination Therapy of IMO-2125 and an Anti-CTLA-4 Antibody FIGS. 7A-E show an evaluation of the antitumor activity of intratumoral IMO-2125 in combination with anti-CTLA-4 mAb on treated tumors and systemic lung metastases. Study design is shown in FIG. 7A and results are shown in FIGS. 7B-E.

BALB/c mice were implanted s.c. with $2\times10^7$ CT26 cells on right flank. The mice were than i.v. injected with $3\times10^6$ CT26 cells to establish lung metastases. Treatment was initiated on day 5. 2.5 mg kg IMO-2125 was administered intratumorally into CT26 solid tumors on the right flank and 10 mg/kg anti-CTLA-4 mAb was administered by interperitoneal (i.p.) injection. IMO-2125 and anti-CTLA-4 mAb were given either alone or co-administered on days 5, 6, 8 and 9. Lungs and T cells from spleens of PBS control, IMO-4, anti-CTLA-4 mAb or IMO-2125 and anti-CTLA-4 mAb treated tumor-bearing mice were collected.

Intratumoral IMO-2125 and anti-CTLA-4 mAb combination demonstrated improved growth inhibition in treated tumors versus monotherapy with either agent.

FIGS. 8A-E show anti-tumor activities of IMO-2125 and anti-CTLA-4 mAb alone or in combination on systemic lung metastasis.

FIGS. 9A-D show that intratumoral IMO-2125 and anti-CTLA-4 mAb combination increased TILs in metastatic nodules.

The combination of intratumoral IMO-2125 and an anti-CTLA-4 mAb resulted in improved inhibition of tumor growth, regression of systemic lung metastases and infiltration of TILs versus monotherapy with either agent. The effects were observed in directly treated tumors and systemic lung metastasis.

Figure 10:
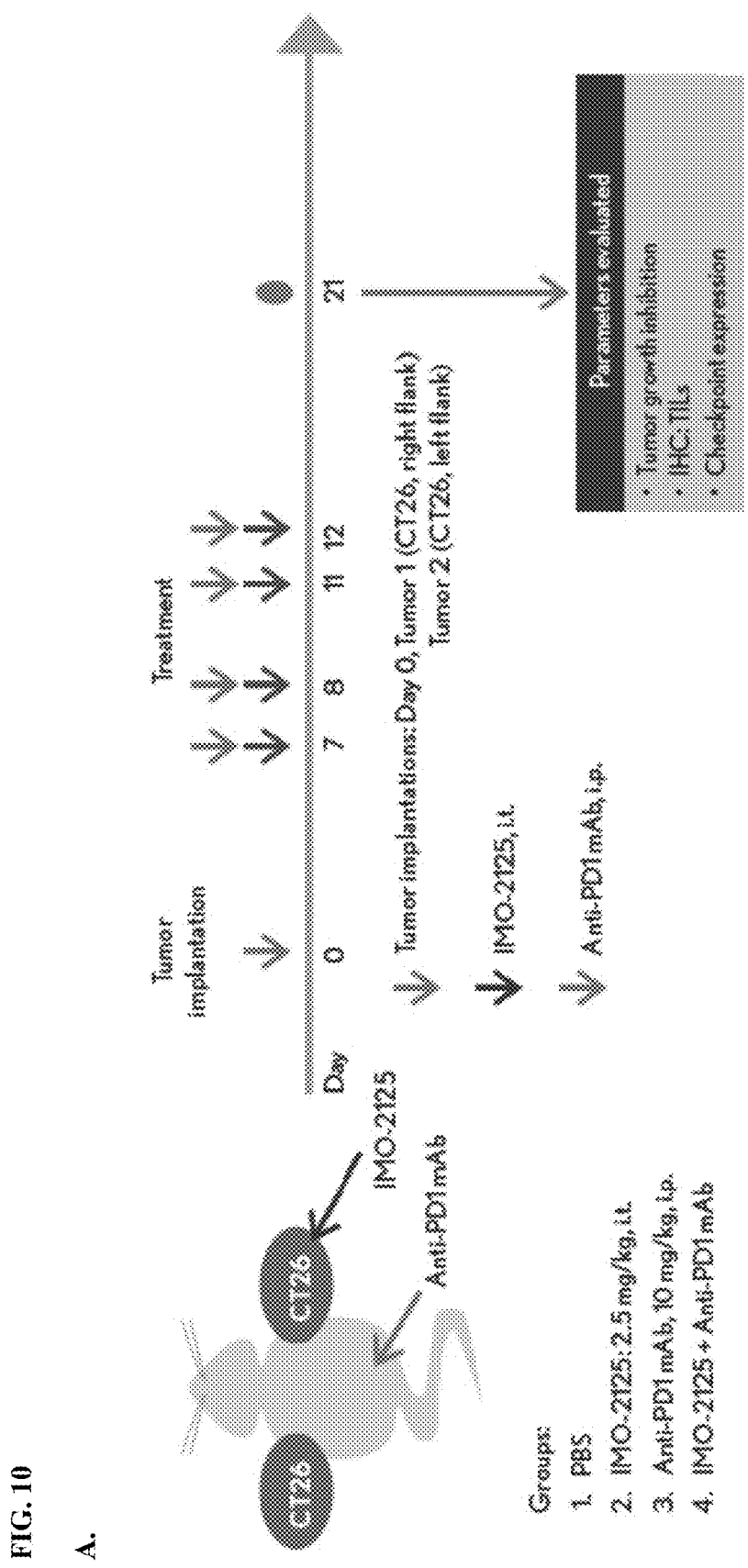
Figure 10:
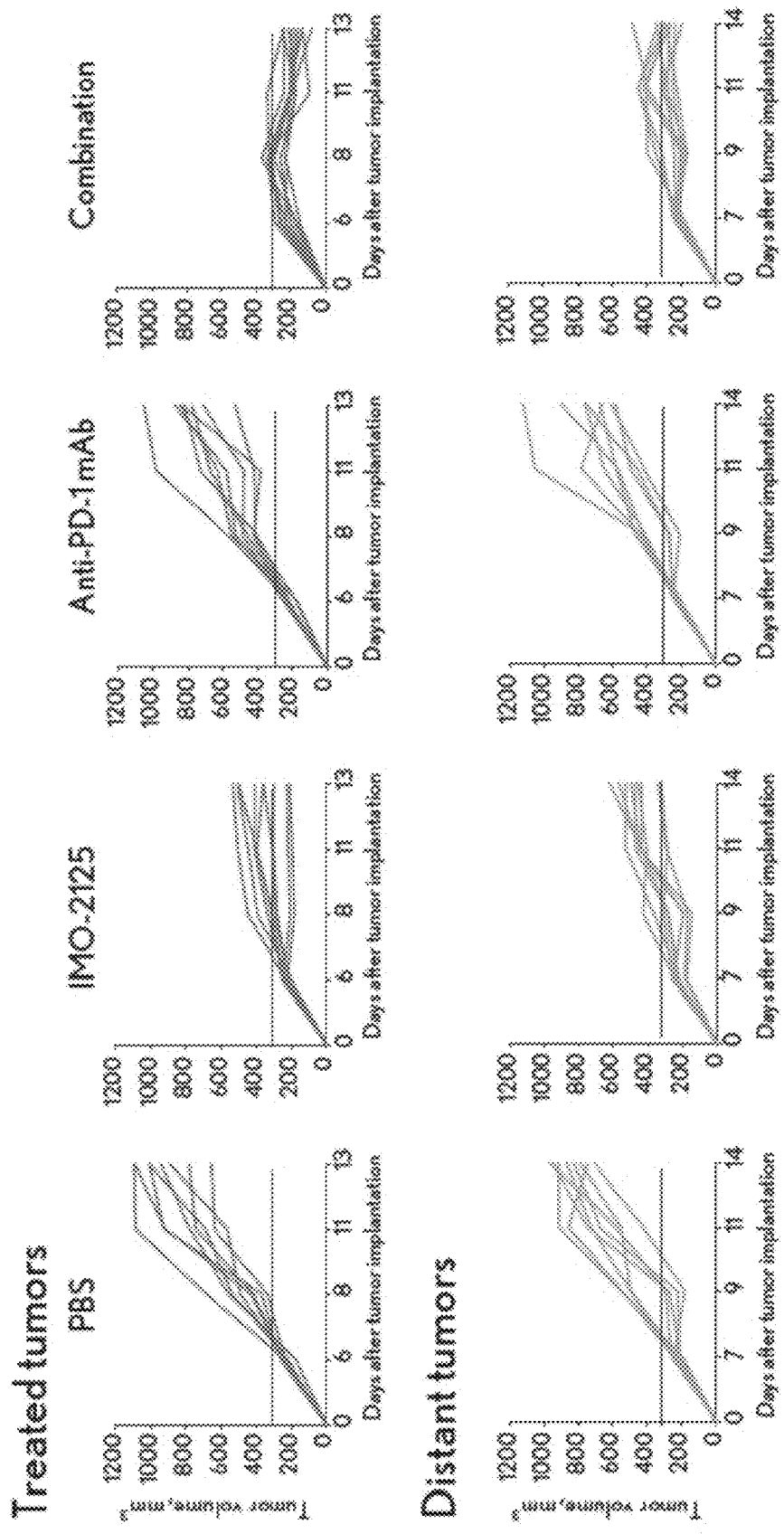
Figure 10:
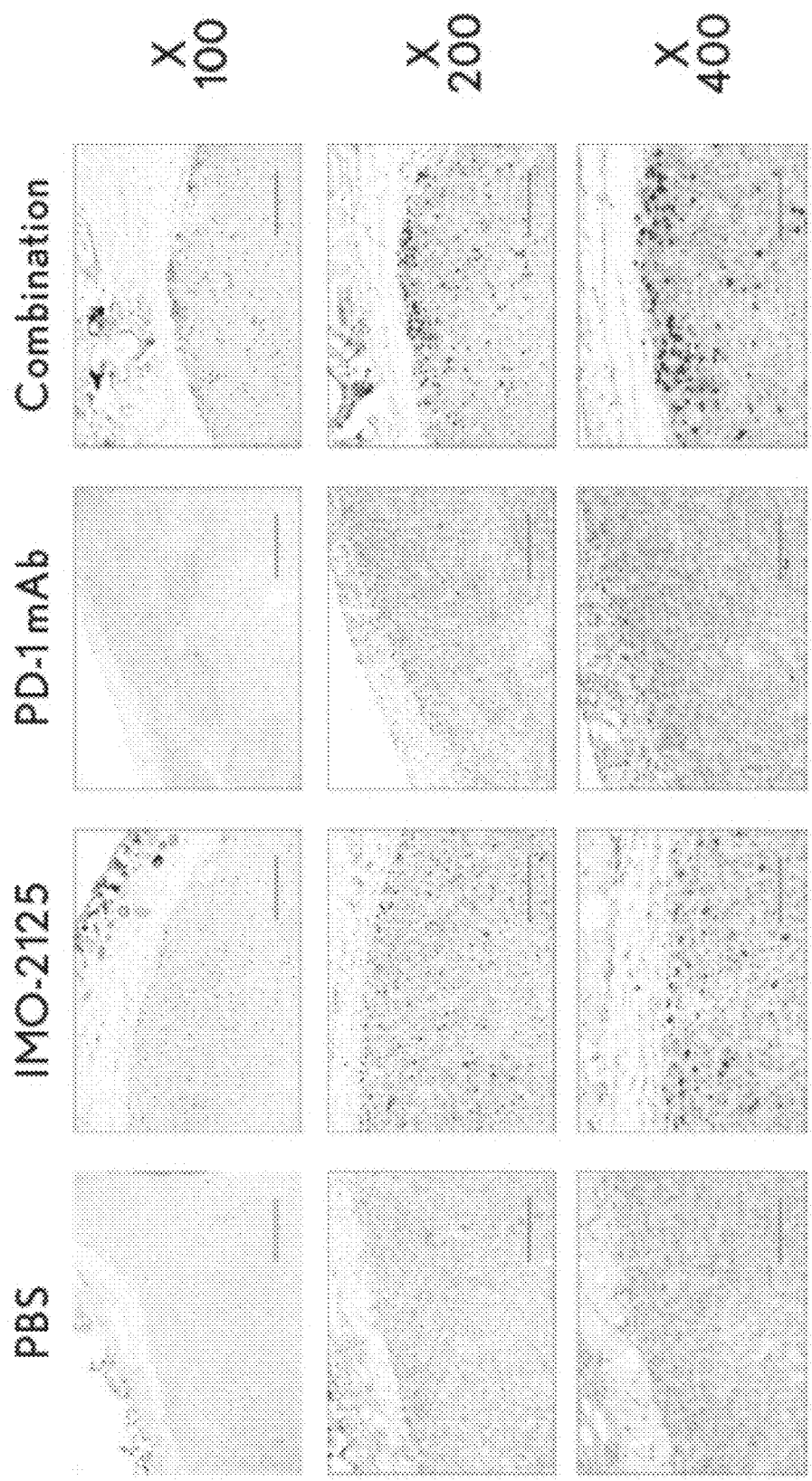
Figure 10:
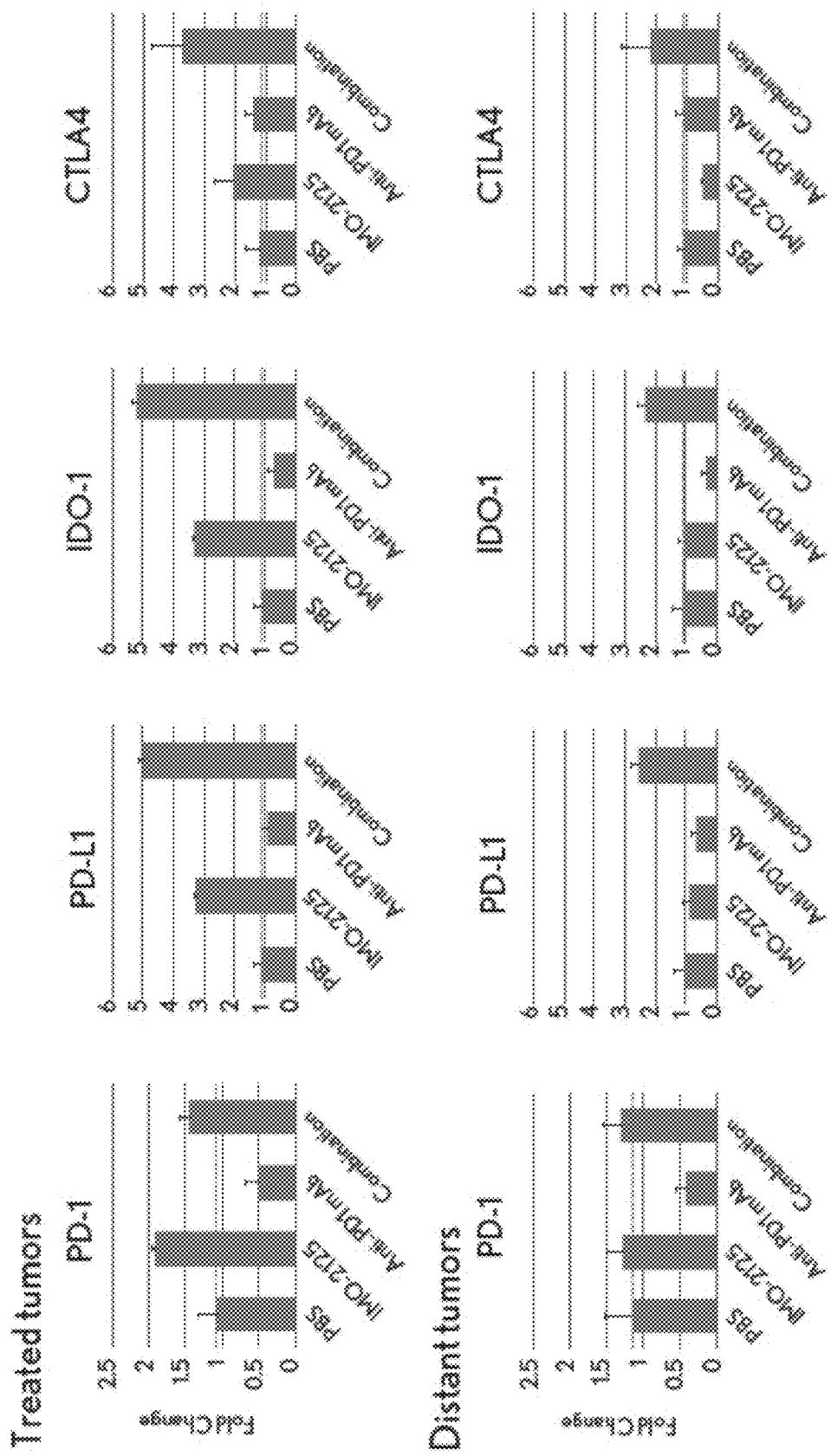

Example 3: Anti-Tumor Effects of Combination Therapy of IMO-2125 and an Anti-PD-1 Antibody FIGS. 10A-R show an evaluation of the antitumor activity of intratumoral IMO-2125 in combination with anti-PD-1 mAb in CT26 colon carcinoma tumor model. FIG. 10A shows the study design. BALB/c mice (n=8 per group) were implanted s.c. with $1\times10^7$ murine colon carcinoma CT26 cells in right flank (Tumor 1) and left flank (Tumor 2). Treatment was initiated on day 7 when tumor volume on reached 200 to 300 mm$^3$. 2.5 mg/kg IMO-2125 (50 µg in 100 µL PBS) was i.t injected at right tumor nodules and anti-PD-1 mAb (10 mg/kg, 200 µg/mouse) was administered by i.p. injection either alone or co-administered on days 7, 8, 11 and 12 for total 4 times. Tumor nodules were collected at day 14. Tumor growth inhibition, TILs and checkpoint gene expression were evaluated at day 21. FIGS. 10B-I show the impact of the combination on tumor growth kinetics at treated and distal sites. The combination of IMO-2125 and anti-PD-1 demonstrated growth inhibition in both treated and distal sites that was superior to either monotherapy. FIG. 10J shows the impact of the combination on TILs. intratumoral IMO-2125 and anti-PD-1 mAb combination increased TILs. The PBS control group showed a few T cells (brown color); the IMO-2125 group showed large number of T cells; the PD-1 mAb group showed slightly increased T cells over PBS treated group; the combination group showed abundant T cells—more than IMO-2125 treated group (magnification: top row×100, mid row×200, bottom row×400). FIGS. 10K-R show checkpoint gene expression at treated and distal sites after treatment with the combination of IMO-2125 and anti-PD-1.

IMO-2124 and anti-PD-1 were tested in combination on treated tumors and systemic lung metastases. See FIGS. 11A-N.

Figure 11:
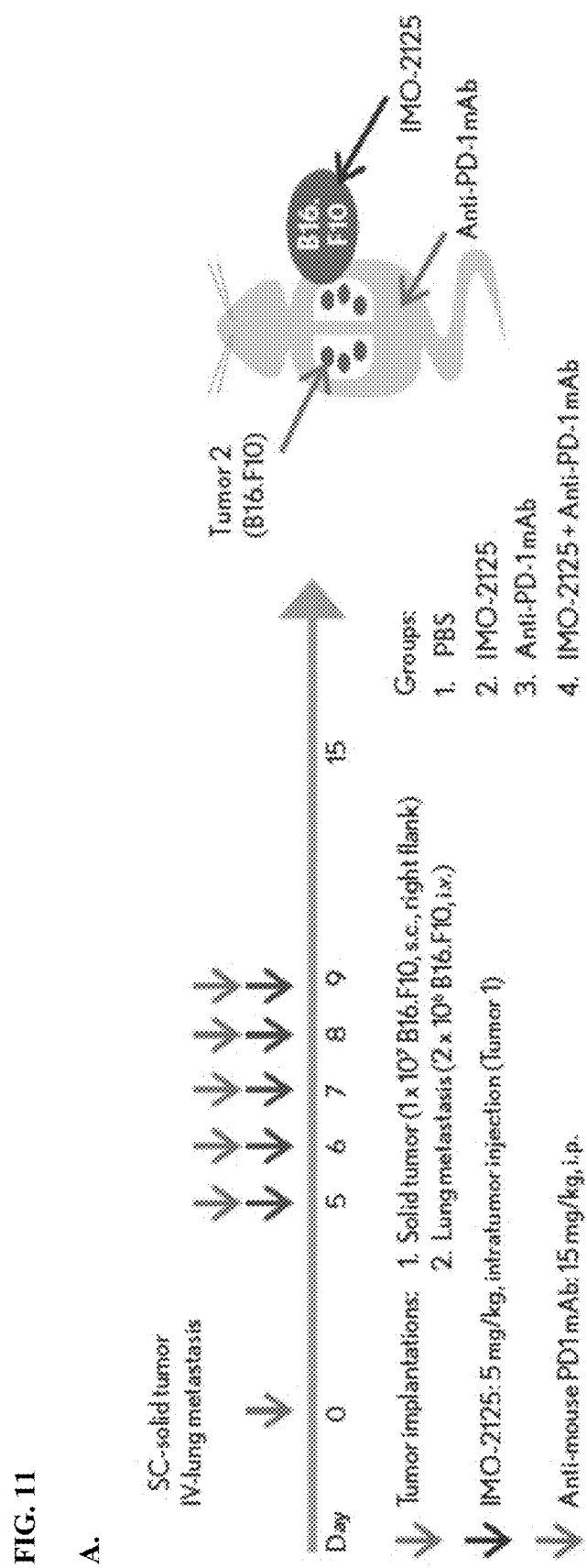
Figure 11:
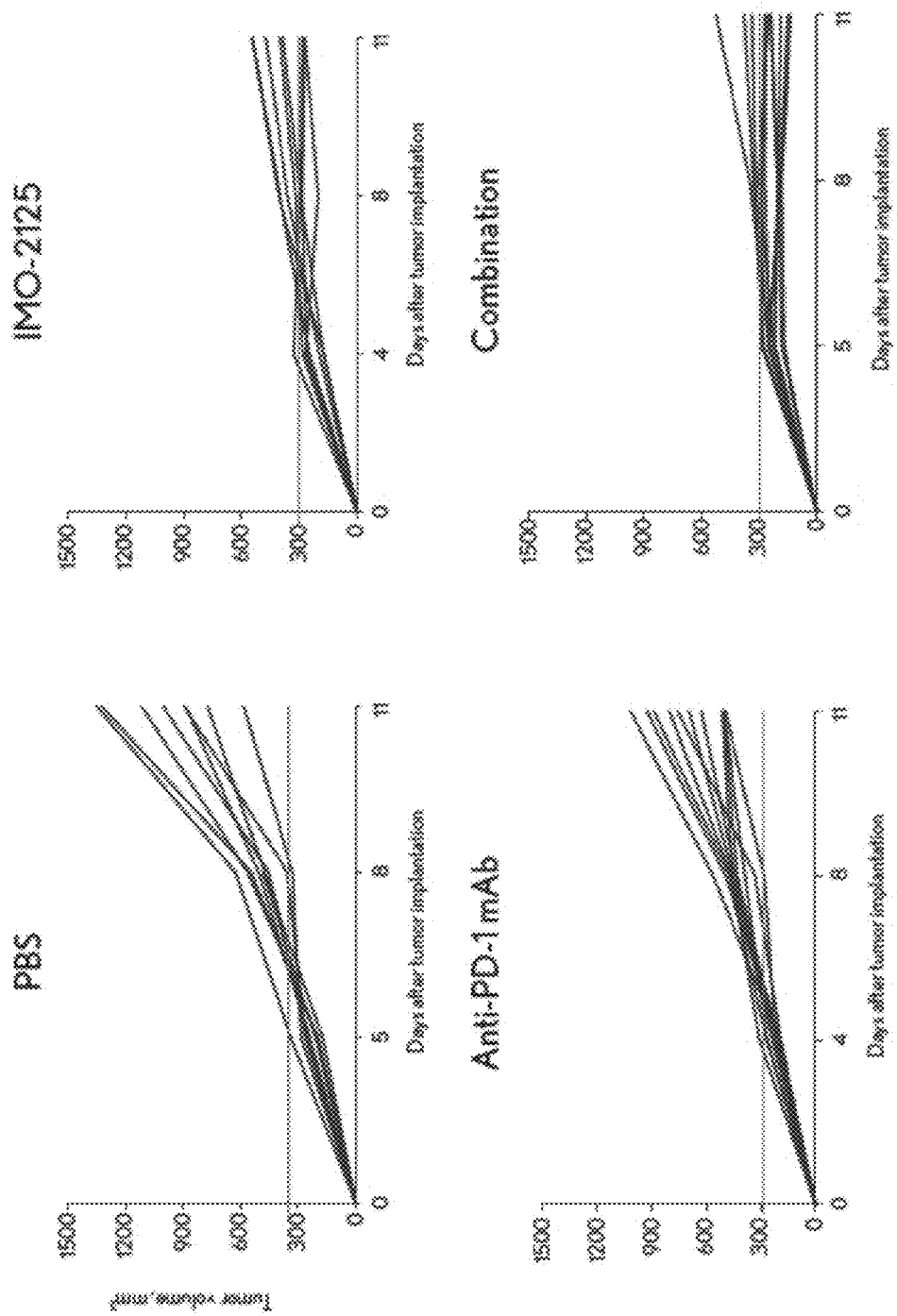
Figure 11:
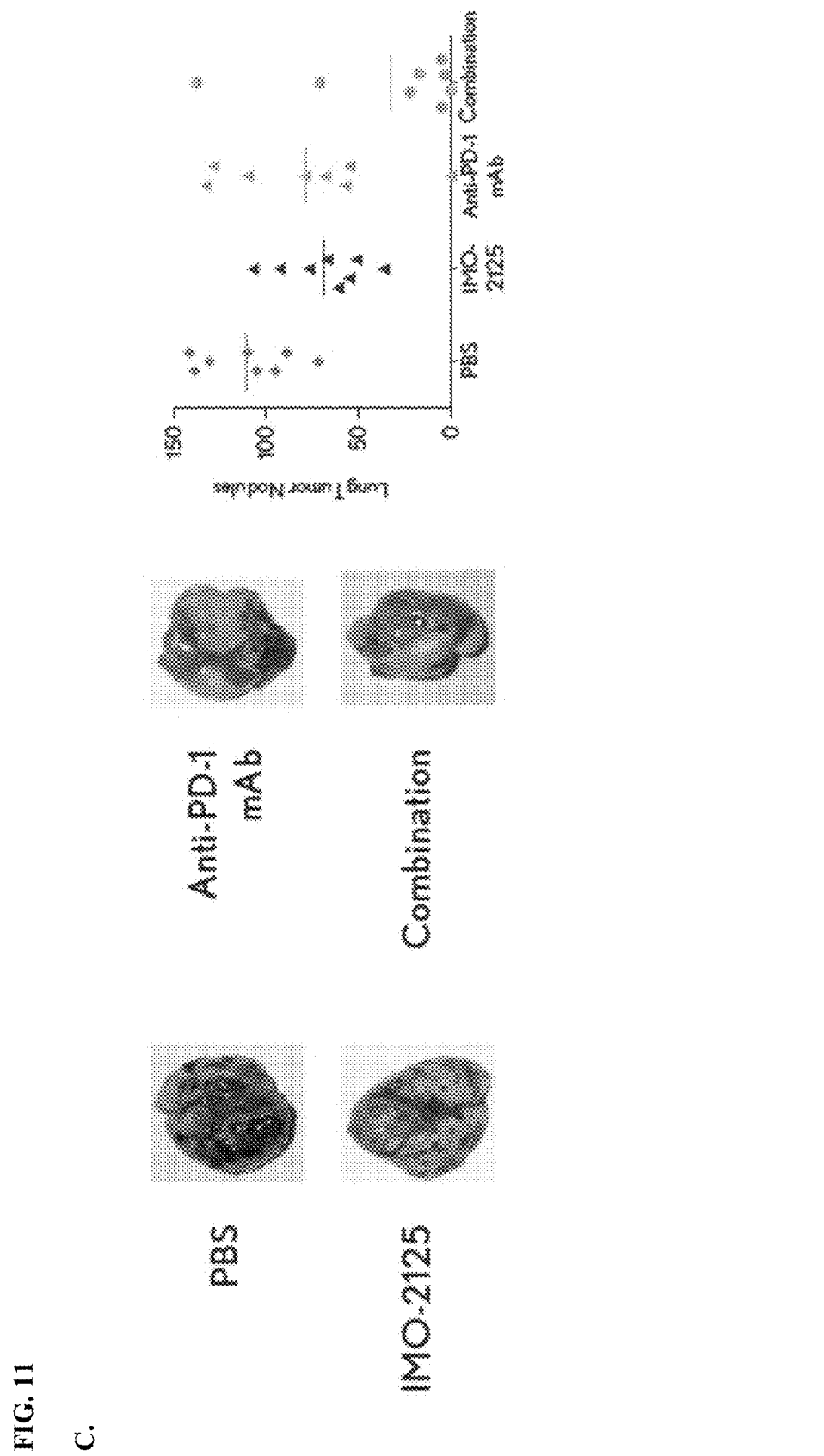

C57BL/6 mice (n=10) were implanted s.c. with $1\times10^7$ B 16.F, 10 cells in the right flank (Tumor 1). The mice were than i.v. injected with $2\times10^6$ B16.F10 cells to establish lung metastases (Tumor 2). Treatment was initiated on day 5. 5 mg/kg IMO-2125 was administered intratumorally into B16 solid tumors on the right flank and 15 mg/kg anti-PD-1 mAb was administered by interperitoneal (i.p.) injection. IMO-2125 and anti-PD-1 mAb were given either alone or co-administered on days 5, 6, 7, 8, and 9. Samples from control, IMO-2125, anti-PD-1 mAb or IMO-2125 and anti-PD-1 mAb treated tumor-bearing mice were collected. FIG. 11A shows the study design.

FIGS. 11B-E show the impact of the combination on tumor growth kinetics at treated sites.

FIGS. 11F-J show the combination's impact on lung metastases. Intratumoral injections of IMO-2125 in combination with anti-PD-1 mAb induced potent systemic immune responses against disseminated lung metastases FIGS. 11K-N show histopathology of metastatic lung tumors (Circle: Large tumor nodule, Arrow: Small tumor nodule, Inset figures: HE stained (×40), and Large figures: CD3 stained (×400)). Treatment with intratumoral IMO-2125 and anti-PD-1 mAb combination led to decreased lung tumor metastasis (inset and large figures) and creased TILs (large figure).

Treatment with a combination of intratumoral IMO-2125 with an anti-PD-1 antibody showed more potent antitumor activity than either agent alone. Antitumor activity was observed on treated as well as distant tumors. Infiltration levels of TILs increased in both treated and distant tumors. In preclinical models, IMO-2125 increased PD-L1 and other checkpoint expression in the treated and distant tumors.

Figure 12:
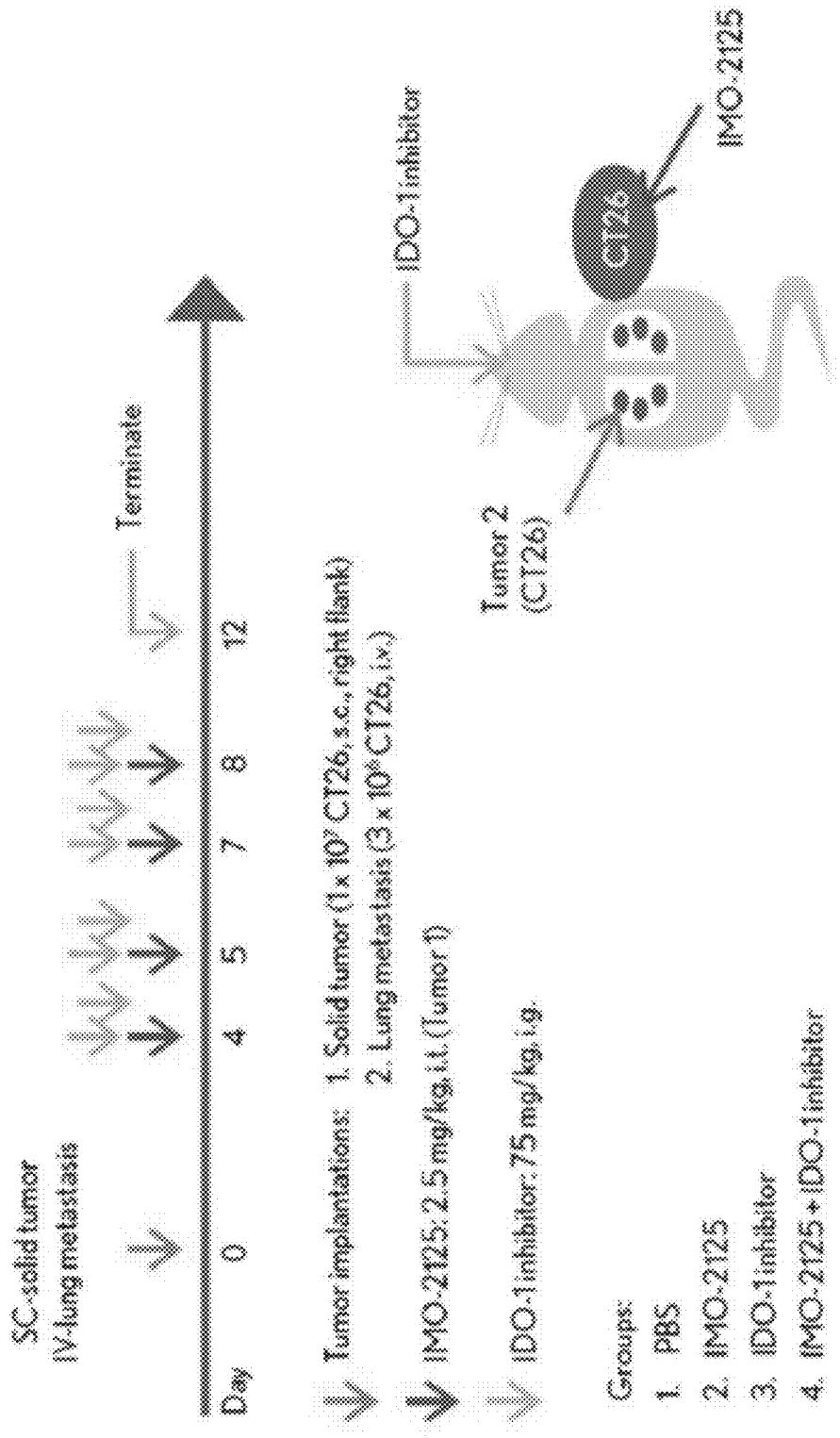
FIG. 12 shows a study design to evaluate the antitumor activity of intratumoral IMO-2125 in combination with an IDO-1 inhibitor on treated tumors and systemic lung metastases.

Example 4: Anti-Tumor Effects of Combination Therapy of IMO-2125 and an IDO-1 Inhibitor FIG. 12 shows a study design to evaluate the antitumor activity of intratumoral IMO-2125 in combination with an IDO-1 inhibitor on treated tumors and systemic lung metastases in a mouse model. Solid tumors and lung metastasis are implanted on Day 0 (solid tumor, $1\times10^7$ CT26, s.c., right flank; lung metastasis, $3\times10^6$ CT26 i.v.), with IMO-2125 given intratumorally (2.5 mg/kg) on Days 4, 5, 7, and 8. An IDO-1 inhibitor is administered twice (75 mg/kg i.g.) on Days 4, 5, 7, and 8.

Figure 13A:
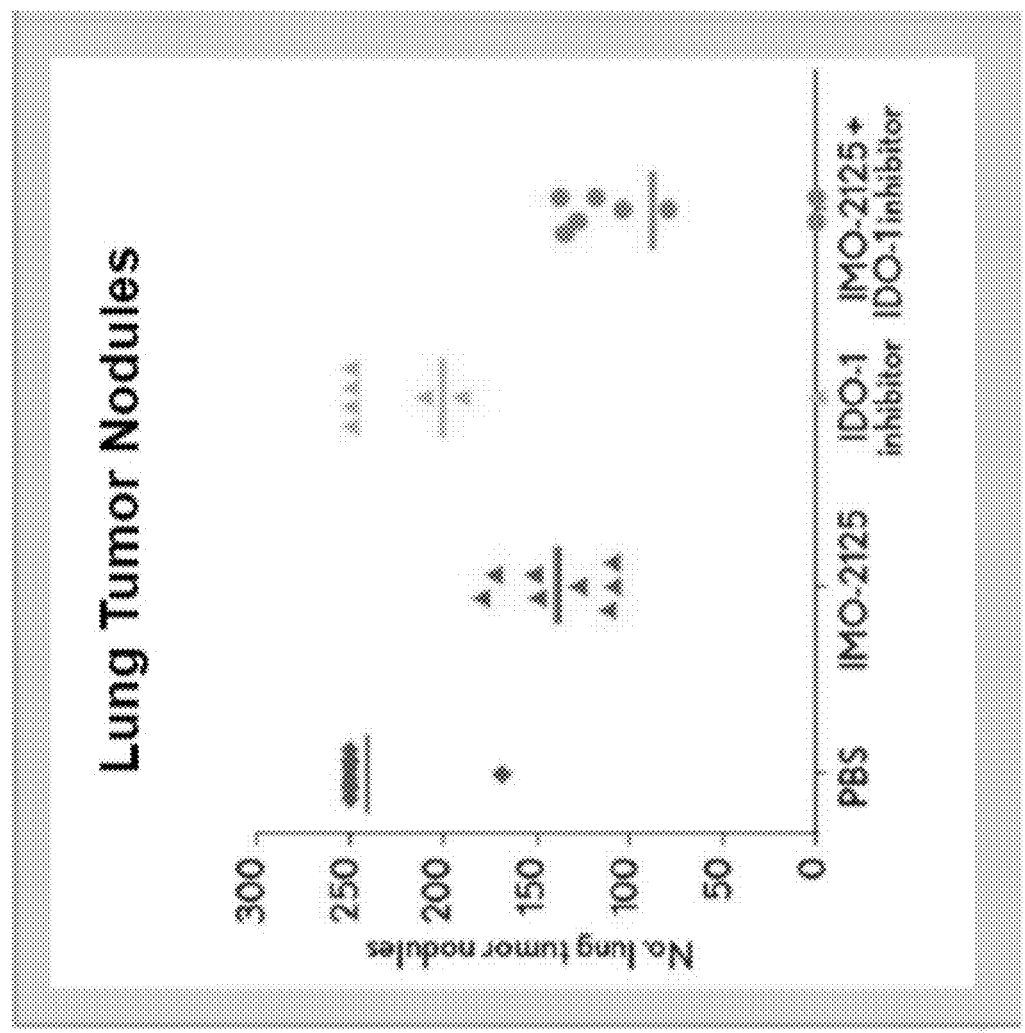
FIGS. 13A-B show that intratumoral IMO-2125 antitumor activity is potentiated by co-treatment with an IDO-1 inhibitor.
Figure 13B:
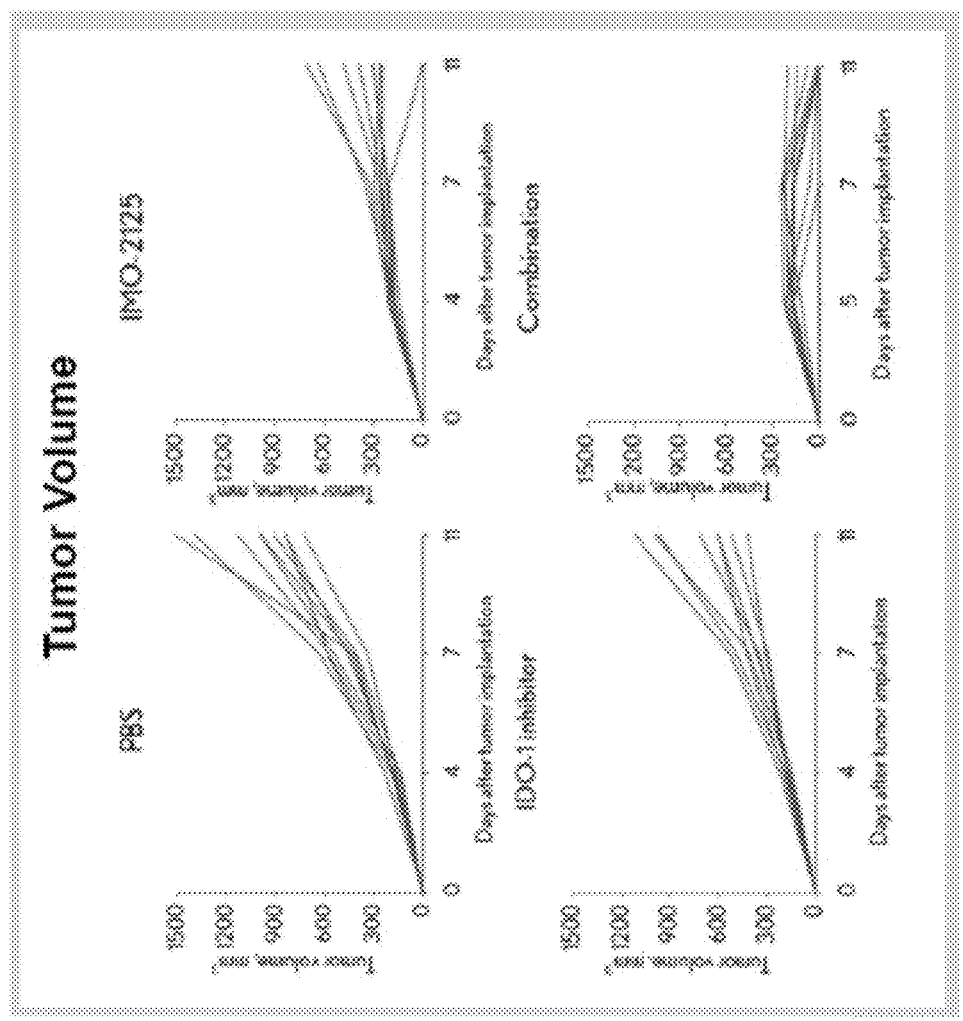

FIGS. 13A-B show that intratumoral IMO-2125 antitumor activity is potentiated by co-treatment with an IDO-1 inhibitor. FIG. 13A shows the number of lung tumor nodules in each treatment group, showing the improvement of IMO- 2125 and IDO-1 inhibitor in comparison to each agent alone. FIG. 13B shows the change in tumor volume in each treatment group during the regimen.

Example 5: Study Population of Adults with Unresectable or Metastatic Melanoma that Progressed with ≥12 Weeks PD-1 Directed Therapy (Alone or in Combination)

Figure 14:
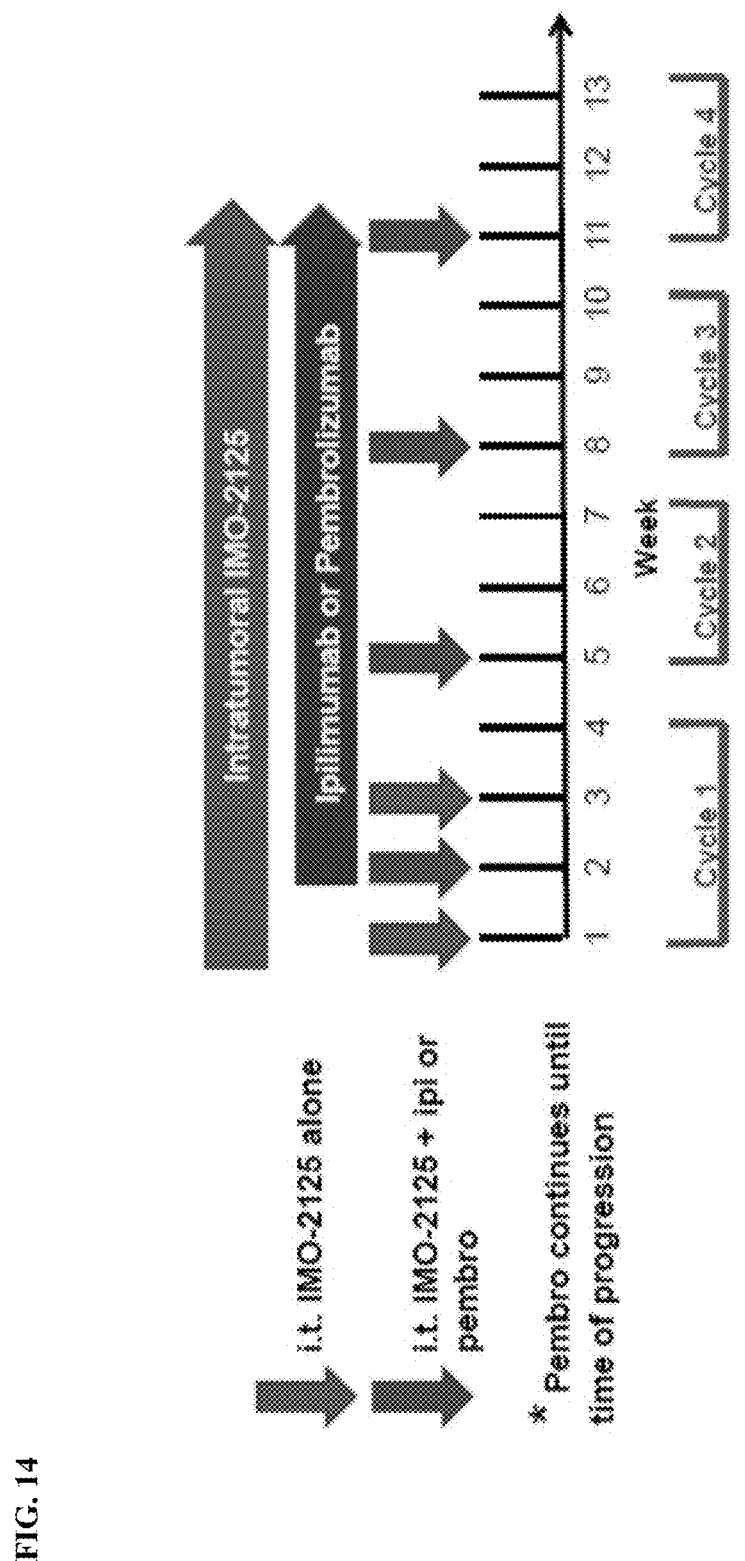
FIG. 14 provides a dosing overview in a study population of adults with unresectable or metastatic melanoma that progressed with ≥12 weeks of PD-1-directed therapy (alone or in combination).

FIG. 14 provides a dosing overview in a study population of adults with unresectable or metastatic melanoma that progressed with ≥12 weeks of PD-1-directed therapy (alone or in combination). IMO-2125 was administered alone, intratumorally, in weeks 1 and 3. IMO-2125 was administered with ipilimumab or pembrolizumab in weeks 2, 5, 8, and 11. Administration of pembrolizumab continues every third week until time of progression.

Figure 15A:
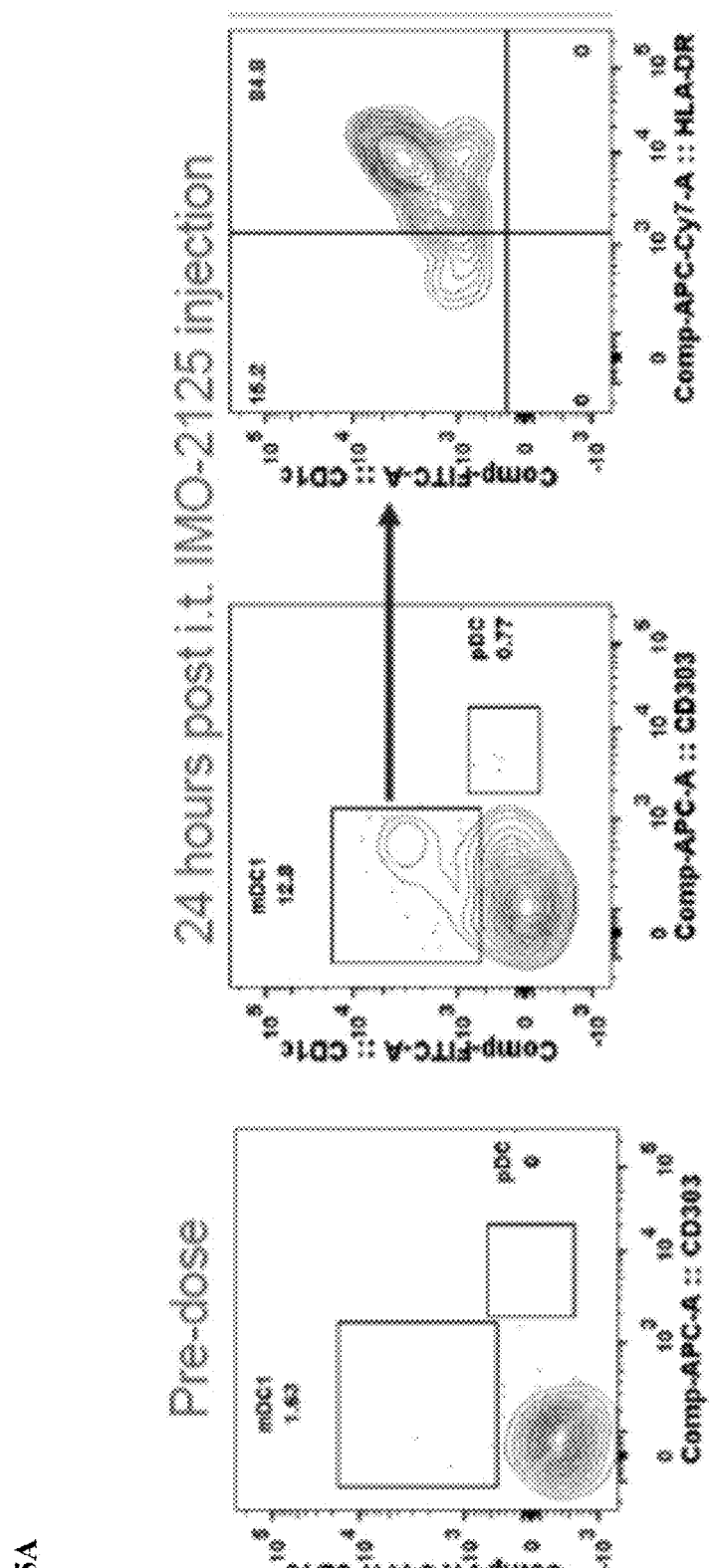
Figure 15B:
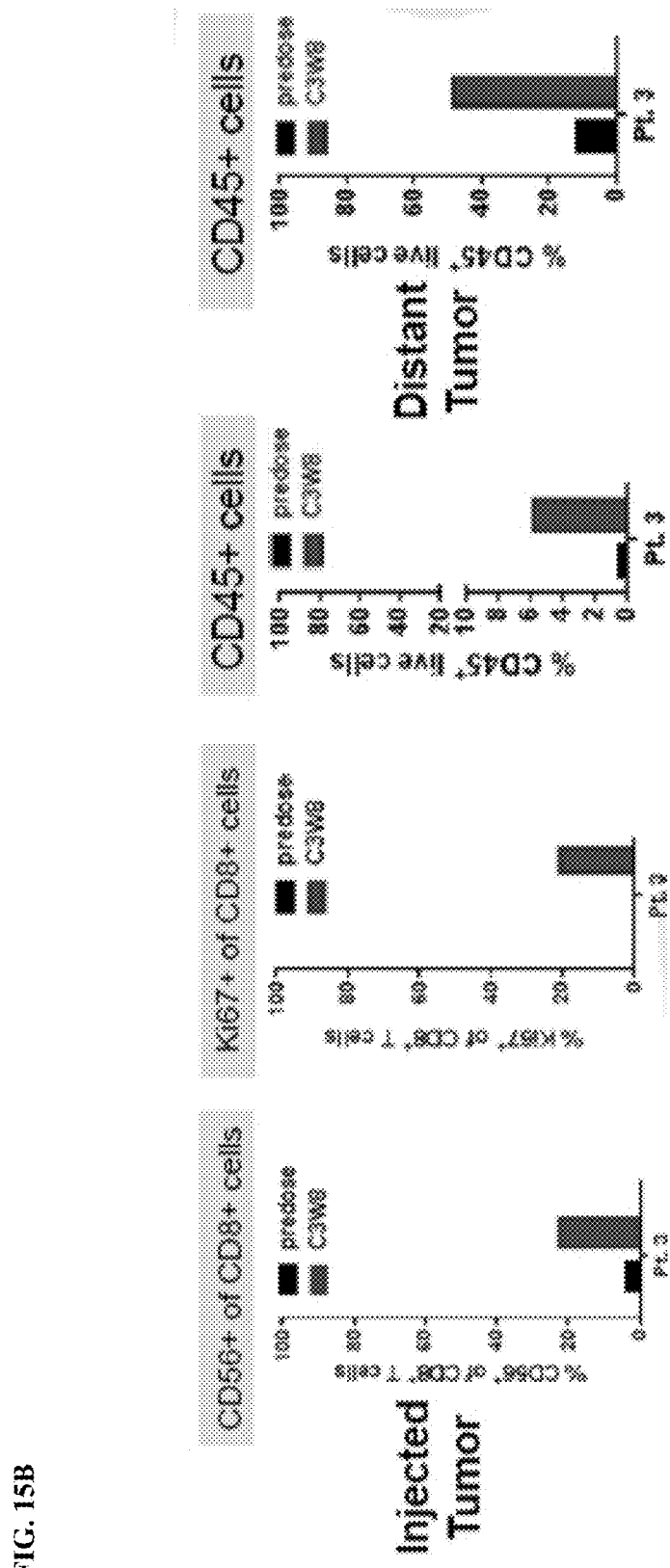

FIGS. 15A-C show dendritic cell maturation results (CD1c, CD303, and HLA-DR expression) and pre-dose and 24 hours post i.t. IMO-2125 injection for patient 003 (4 mg doses of IMO-2125; ipilimumab); and FIGS. 15D-G show T-cell activation results in injected and distant tumors.

Figure 16:
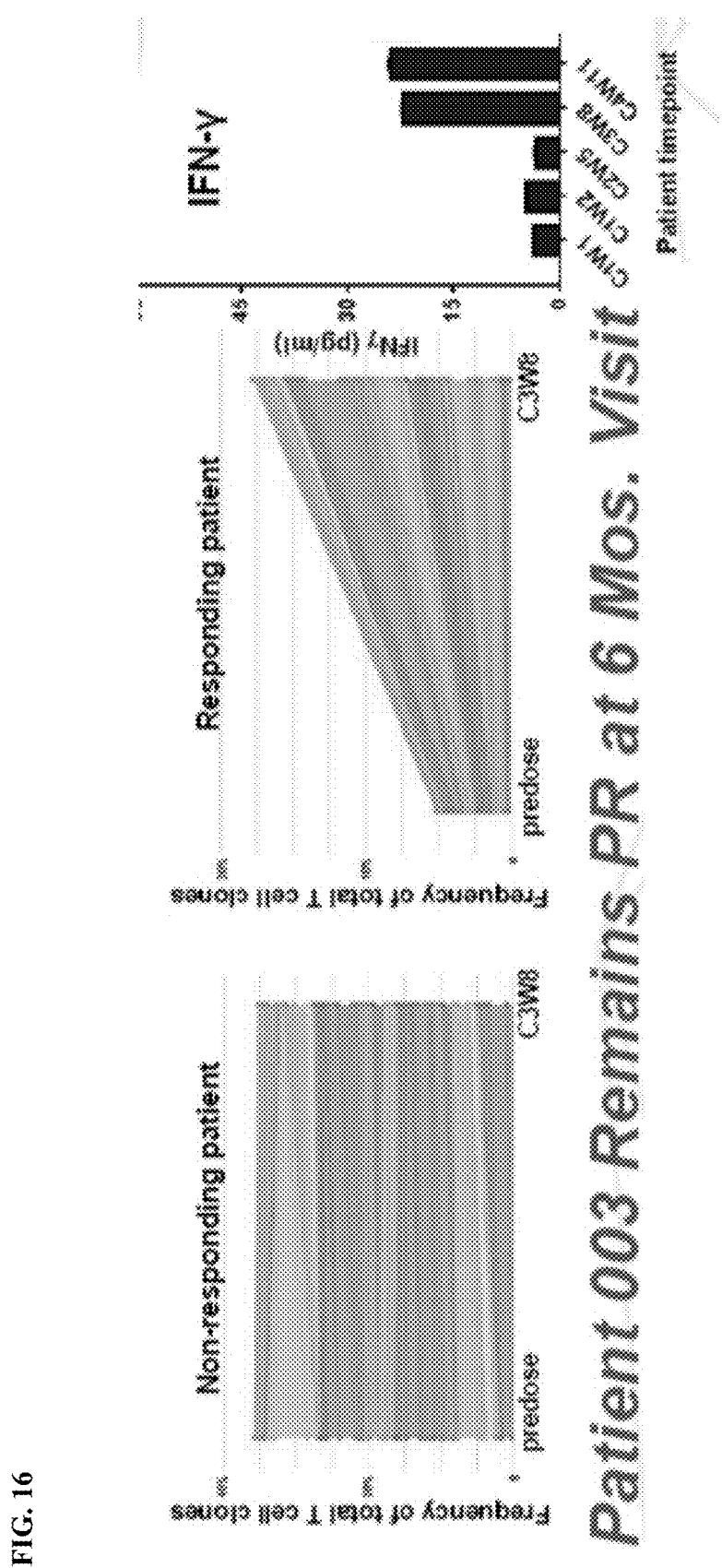
FIGS. 16A-C show expansion of top cell clones in distant lesions and induction of IFN-γ for patient 003 (4 mg IMO-2125).

FIGS. 16A-C show expansion of top cell clones in distant lesions, and compares a non-responding patient with a responding patient (patient 003, 4 mg IMO-2125, ipilimumab). The far right panel shows inductions of IFN-γ for patient 003.

Figure 17:
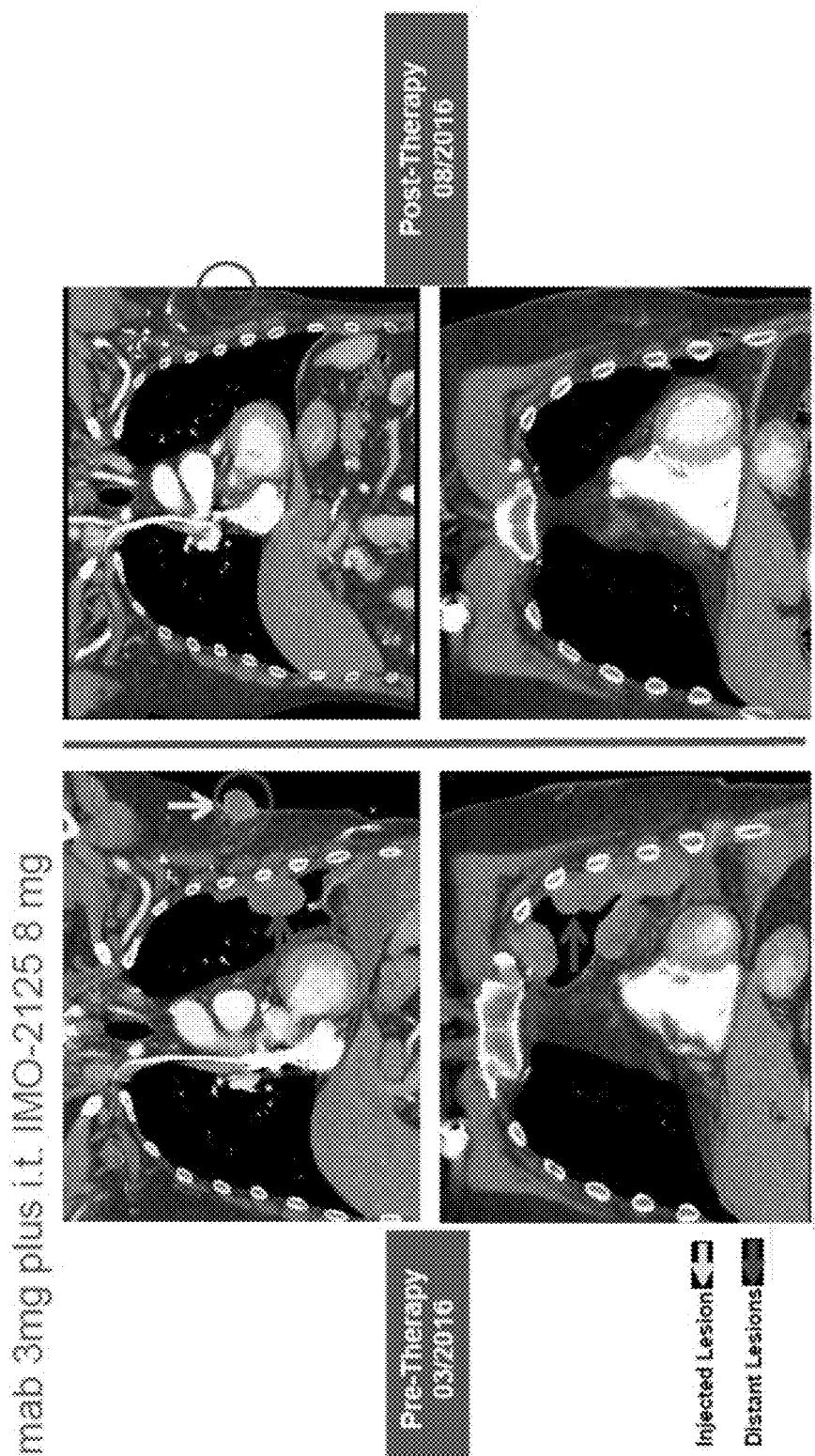
FIG. 17 shows tumor imaging pre- and post-therapy for patient 004 (8 mg 2125).

FIG. 17 shows tumor imaging pre- and post-therapy for patient 004 (8 mg 2125, 3 mg ipilimumab). Injected and distant lesions are not visible after about 5 weeks of therapy.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A method for treating a cancer patient, comprising intratumorally administering IMO-2125 to a melanoma patient, and administering an immune checkpoint inhibitor therapy that targets CTLA-4, PD-1, or PD-L1 to the patient beginning about one or two weeks after the initial IMO-2125 dose.

2. The method of claim 1, wherein the patient is unresponsive or became resistant to prior treatment with PD-1 blockade therapy.

3. The method of claim 2, wherein the prior PD-1 blockade therapy includes therapy with nivolumab or pembrolizumab.

4. The method of claim 1, wherein the cancer is a primary cancer or a metastatic cancer.

5. The method of claim 1, wherein the cancer is metastatic melanoma.

6. The method of claim 1, wherein the IMO-2125 is administered intratumorally at from about 4 mg to about 64 mg per dose.

7. The method of claim 6, wherein the IMO-2125 is administered intratumorally at from about 4 to about 12 mg per dose.

8. The method of claim 6, wherein the IMO-2125 is administered intratumorally at about 8 mg per dose.

9. The method of claim 1, wherein about 3 to about 12 doses of IMO-2125 are administered.

10. The method of claim 9, wherein about 4 to about 8 doses of IMO-2125 are administered over 10 to 12 weeks.

11. The method of claim 10, wherein about 6 doses of IMO-2125 are administered over 10 to 12 weeks.

12. The method of claim 9, wherein therapy is initiated with 3 to 5 weekly doses of IMO-2125, followed by 3 to 8 maintenance doses administered about every three weeks.

13. The method of claim 12, wherein the IMO-2125 is administered in weeks 1, 2, 3, 5, 8, and 11.

14. The method of claim 1, wherein the patient receives an anti-CTLA-4 agent beginning on week 2 or week 3 after the initial IMO-2125 agonist dose.

15. The method of claim 14, wherein the anti-CTLA-4 agent is administered from 2 to 6 times, and optionally about 4 times.

16. The method of claim 15, wherein the anti-CTLA-4 agent is administered every three weeks.

17. The method of claim 14, wherein the anti-CTLA-4 agent is ipilimumab.

18. The method of claim 1, wherein the patient receives an anti-PD-1 agent beginning on week 2 or week 3 after the initial IMO-2125.

19. The method of claim 18, wherein the anti-PD-1 agent is administered from 2 to 6 times, and optionally about 4 times.

20. The method of claim 19, wherein the anti-PD-1 agent is administered every three weeks.

21. The method of claim 18, wherein the anti-PD-1 agent is pembrolizumab or nivolumab.

22. The method of claim 1, wherein the immune checkpoint inhibitor therapy is administered parenterally, and optionally by intravenous infusion, subcutaneous injection, or intratumoral injection.

23. A method for treating metastatic melanoma, comprising administering IMO-2125 intratumorally to a metastatic melanoma patient previously found to be unresponsive or only partially responsive to PD-1 blockade therapy; the IMO-2125 being administered at a dose of from 4 to 32 mg per dose in weeks 1, 2, 3, 5, 8, and 11; with ipilimumab or pembrolizumab administered intravenously at from 2 to 4 mg/kg every three weeks beginning in week 2.

24. A method for treating a metastatic melanoma patient, comprising:
(i) intratumorally administering a dose of between 4 mg to 32 mg of IMO-2125;
(ii) administering an immune checkpoint inhibitor therapy selected from nivolumab, pembrolizumab, ipilimumab, and tremelimumab,
wherein the immune checkpoint inhibitor therapy is administered to the patient about one or two weeks after the initial IMO-2125 dose.

* * * * *